US009175153B2

(12) United States Patent
Trexler et al.

(10) Patent No.: US 9,175,153 B2
(45) Date of Patent: Nov. 3, 2015

(54) CELLULOSE HYDROGEL COMPOSITIONS AND CONTACT LENSES FOR CORNEAL APPLICATIONS

(71) Applicant: The Johns Hopkins University, Baltimore, MD (US)

(72) Inventors: Morgana M. Trexler, Baltimore, MD (US); Jenna L. Graham, Columbia, MD (US); Jennifer L. Breidenich, Atlanta, GA (US); Jeffrey P. Maranchi, Clarkburg, MD (US); Julia B. Patrone, Ellicott City, MD (US); Marcia W. Patchan, Columbia, MD (US); Jennifer H. Elisseeff, Baltimore, MD (US); Xiomara Calderon-Colon, Laurel, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/483,637

(22) Filed: Sep. 11, 2014

(65) Prior Publication Data
US 2015/0044446 A1 Feb. 12, 2015

Related U.S. Application Data

(63) Continuation-in-part of application No. 13/295,515, filed on Nov. 14, 2011, and a continuation-in-part of application No. 13/197,116, filed on Aug. 3, 2011, now Pat. No. 8,871,016.

(60) Provisional application No. 61/450,251, filed on Mar. 8, 2011.

(51) Int. Cl.
C08L 1/02 (2006.01)
G02B 1/04 (2006.01)
(Continued)

(52) U.S. Cl.
CPC ............. *C08L 1/02* (2013.01); *B29D 11/00096* (2013.01); *C08B 1/003* (2013.01); *C08J 3/075* (2013.01); *G02B 1/043* (2013.01);
(Continued)

(58) Field of Classification Search
None
See application file for complete search history.

(56) References Cited

U.S. PATENT DOCUMENTS 5,480,427 A 1/1996 Kelman et al.
5,836,313 A 11/1998 Perez et al.
(Continued)

OTHER PUBLICATIONS

Friedlander, P. et al., "Effects of Soft Contacts of Differing Thickness on Corneal Wound Healing in Rabbits," Investigative Ophthalmology & Visual Science, vol. 30, No. 10, 1989, pp. 2138-2147.

*Primary Examiner* — Melvin C Mayes
*Assistant Examiner* — Stefanie Cohen
(74) *Attorney, Agent, or Firm* — Noah J. Hayward

(57) ABSTRACT

The present invention provides cellulose hydrogels having one or more of the following properties: high water content, high transparency, high oxygen permeability, high biocompatibility, high tensile strength and desirable thermal stability. The present invention further provides a process for preparing a cellulose hydrogel comprising (i) a step of activating cellulose, in which the activating step comprises contacting the cellulose with a solvent to activate the cellulose for a time duration from about 2 hours to about 30 hours; (ii) substantially dissolving the activated cellulose to form a solution; and (iii) gelling the solution to form a gel, in which the gelling step comprises allowing the solution to gel in an environment comprising a relative humidity from about 30% to about 80% at 35° C.

20 Claims, 32 Drawing Sheets

(51) Int. Cl.

| | | |
|---|---|---|
| *C08B 1/00* | (2006.01) | |
| *C08J 3/075* | (2006.01) | |
| *G02C 7/04* | (2006.01) | |
| *B29D 11/00* | (2006.01) | |
| C08L 33/06 | (2006.01) | |
| C08L 33/20 | (2006.01) | |
| C08L 33/26 | (2006.01) | |
| A61F 2/14 | (2006.01) | |

(52) U.S. Cl.
CPC ............... *G02C 7/049* (2013.01); *A61F 2/145* (2013.01); *C08J 2301/02* (2013.01); *C08L 33/066* (2013.01); *C08L 33/20* (2013.01); *C08L 33/26* (2013.01); *C08L 2205/16* (2013.01)

(56) References Cited

U.S. PATENT DOCUMENTS

| | | | |
|---|---|---|---|
| 5,846,213 A | 12/1998 | Wan | |
| 5,962,005 A * | 10/1999 | Saga et al. | 424/424 |
| 6,867,245 B2 | 3/2005 | Iwata et al. | |
| 7,195,912 B2 | 3/2007 | Takezawa et al. | |
| 7,476,398 B1 | 1/2009 | Doillon et al. | |
| 7,544,368 B2 | 6/2009 | Hsu et al. | |
| 7,832,857 B2 * | 11/2010 | Levinson et al. | 351/159.33 |
| 7,857,447 B2 | 12/2010 | Myung et al. | |
| 7,857,849 B2 | 12/2010 | Myung et al. | |
| 7,862,831 B2 | 1/2011 | Wang et al. | |
| 8,357,760 B2 * | 1/2013 | Qiu | 525/327.4 |
| 2003/0170308 A1 | 9/2003 | Cleary et al. | |
| 2004/0142019 A1 | 7/2004 | Serafica et al. | |
| 2006/0134170 A1 | 6/2006 | Griffith et al. | |
| 2006/0246113 A1 | 11/2006 | Griffith et al. | |
| 2008/0069857 A1 | 3/2008 | Yeo et al. | |
| 2008/0145426 A1 | 6/2008 | Amundson et al. | |
| 2008/0317818 A1 | 12/2008 | Griffith et al. | |
| 2010/0010187 A1 | 1/2010 | Elisseeff | |
| 2010/0080840 A1 | 4/2010 | Cho et al. | |
| 2010/0198348 A1 | 8/2010 | Hiles et al. | |
| 2013/0032059 A1 * | 2/2013 | Trexler et al. | 106/164.01 |

* cited by examiner

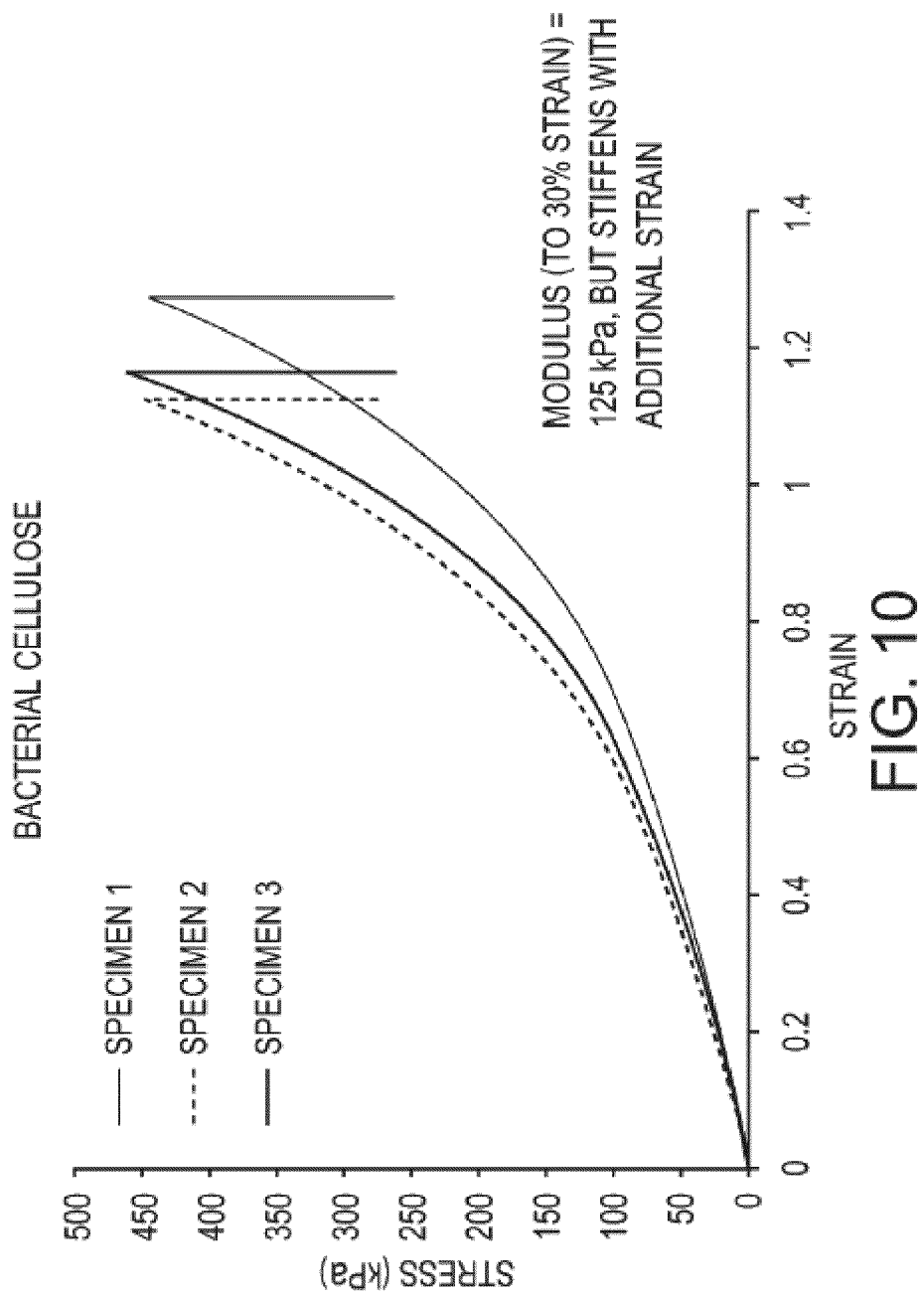

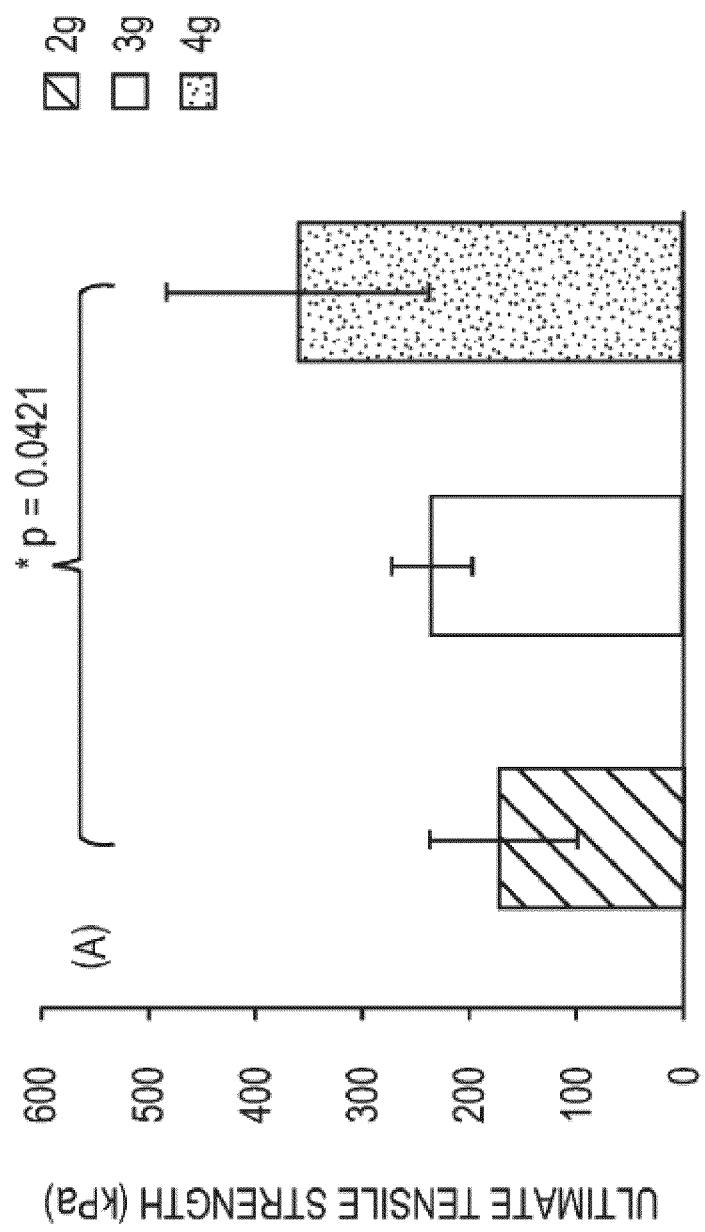

| Material | Average Permeability (Dk) (Barrer) |
|---|---|
| 5% Avicel 101 | 94 |
| 5% MCC4 | 74 |
| 0.5% BC | 60 |
| Commercial Contact Lens Range* | 21-140 |

Average oxygen permeability values for the hydrogels versus commercial contact lenses.

*French, K. (2005). *Optician*, *230*(6030), 16-21.

CELLULOSE HYDROGEL COMPOSITIONS AND CONTACT LENSES FOR CORNEAL APPLICATIONS

CROSS REFERENCE TO RELATED APPLICATIONS

This application is a continuation-in-part of U.S. patent application Ser. No. 13/295,515, filed Nov. 14, 2011, which claims the benefit of prior filed U.S. Provisional Application No. 61/450,251, filed Mar. 8, 2011. This application is a continuation-in-part of U.S. patent application Ser. No. 13/197,116, filed Aug. 3, 2011, now U.S. Pat. No. 8,871,016. Each of U.S. patent application Ser. No. 13/197,116, now U.S. Pat. No. 8,871,016, U.S. patent application Ser. No. 13/295,515, and U.S. Provisional Application No. 61/450,251 is incorporated herein by reference in their entirety.

STATEMENT OF GOVERNMENTAL INTEREST

This invention was made with government support under contract number W81XWH-09-2-0173 awarded by the Department of Defense (DoD) Congressionally Directed Medical Research Programs (CDMRP). The government has certain rights in the invention.

TECHNICAL FIELD

The presently-disclosed invention relates generally to cellulose hydrogels and processes for their production. The presently-disclosed invention also relates to applications of cellulose hydrogels, for example, as ophthalmic materials, such as soft contact lenses suitable for treatment of ocular wounds.

BACKGROUND

Hydrogels are water-insoluble polymers having the ability to swell in water or aqueous solution without dissolution and to retain a significant portion of water or aqueous solution within their structure. Hydrogels possess a degree of flexibility similar to natural tissue. As such, hydrogels have many uses and applications.

Attempts have been made to improve upon various properties of hydrogels, for example, to increase strength, water content, transparency, permeability or biocompatibility properties, often with mixed results. For example, attempts have been made to optimize certain physical properties of hydrogels, such as strength, to suit various applications. However, such increases in strength often come at the expense of other properties of the hydrogel, such as transparency or water content.

There remains a need for improved hydrogels that have desirable properties, including some or all of high water content, biocompatibility, tensile strength, oxygen permeability, and transparency to support a variety of uses, including as ophthalmic materials, such as contact lenses.

This background information is provided for the purpose of making information believed by the applicant to be of possible relevance to the present invention. No admission is necessarily intended, nor should it be construed, that any of the preceding information constitutes prior art against the present invention.

BRIEF SUMMARY

One aspect of the invention provides cellulose hydrogels which possess desirable properties, including one or more of the following properties: high water content, high transparency, high oxygen permeability, high biocompatibility, high tensile strength, high thermal stability, and desirable thickness.

Certain embodiments according to the present invention provide a wet cellulose hydrogel exhibiting a range of beneficial properties for use as contact lenses, for example, for use as a corneal bandage. In certain embodiments, the wet cellulose hydrogels comprise a cellulose content from about 1% to about 10% by weight. Moreover, the wet cellulose hydrogels according to certain embodiments of the present invention comprise one or more properties selected from the group consisting of: (i) a tensile strength in the range of from about 50 kPa to about 4000 kPa; (ii) a tear strength of from about 0.10 N/mm to about 3 N/mm; (iii) a transparency that exceeds 85% at 550 nm; (iv) Young's modulus of from about 100 kPa to about 1600 kPa; and an oxygen permeability from about 55 to about 150 Dk.

In accordance with certain embodiments of the present invention, the wet cellulose hydrogel comprises a contact lens. Such contact lenses, according to certain embodiments, can be suitable for use as corneal bandage and/or delivery of active agents for the treatment of ocular wounds.

In another aspect, the invention provides a commercial package comprising one or more cellulose hydrogels, together with instructions, for example, for their use. In certain embodiments, the hydrogels are provided in commercial packages and kits, etc., containing contact lenses made in accordance with certain embodiments of the present invention.

In another aspect, the present invention provides a process for preparing a wet cellulose hydrogel. In certain embodiments, the process for preparing a wet cellulose hydrogel comprises: (i) activating the cellulose, wherein the activating step comprises contacting the cellulose with a solvent to activate the cellulose for a time duration from about 2 hours to about 30 hours; (ii) substantially dissolving the activated cellulose to form a solution; and (iii) gelling the solution to form a gel, wherein the gelling step comprises allowing the solution to gel in an environment comprising a relative humidity from about 30% to about 80% at 35° C.

In accordance with certain embodiment, the activating step comprises contacting the cellulose with the solvent to activate the cellulose for about 10 hours to about 20 hours. In certain embodiments, the gelling step comprises allowing the solution to gel in an environment comprising a relative humidity from about 70% to about 80% at 35° C.

Certain embodiments according to the present invention can comprise gelling (or allowing to gel) the cellulose solution in a mold, in which the gelled material (e.g., wet hydrogel) is later removed and optionally washed. In certain embodiments, the mold is a contact lens mold.

BRIEF DESCRIPTION OF THE DRAWING(S)

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

FIGS. 1A-B show cellulose hydrogel microstructure of Avicel 101 and MCC 4 dried by critical point drying following dehydration in methanol.

FIG. 2 shows Fourier Transform Infrared Spectroscopy (FTIR) of wet cellulose hydrogels.

FIGS. 3A-B show thermogravimetric analysis (TGA) of various cellulose hydrogels. FIG. 3A shows the water content of wet Avicel 101 gels as a function of grams of cellulose (per 100 ml of solvent) used in synthesis. FIG. 3B shows TGA analysis of an Avicel 101 hydrogel (made using 5 grams of cellulose per 100 ml solvent).

FIGS. 4A-B show X-ray diffraction of various cellulose powders and cellulose hydrogels.

Figures 7A, 7B:
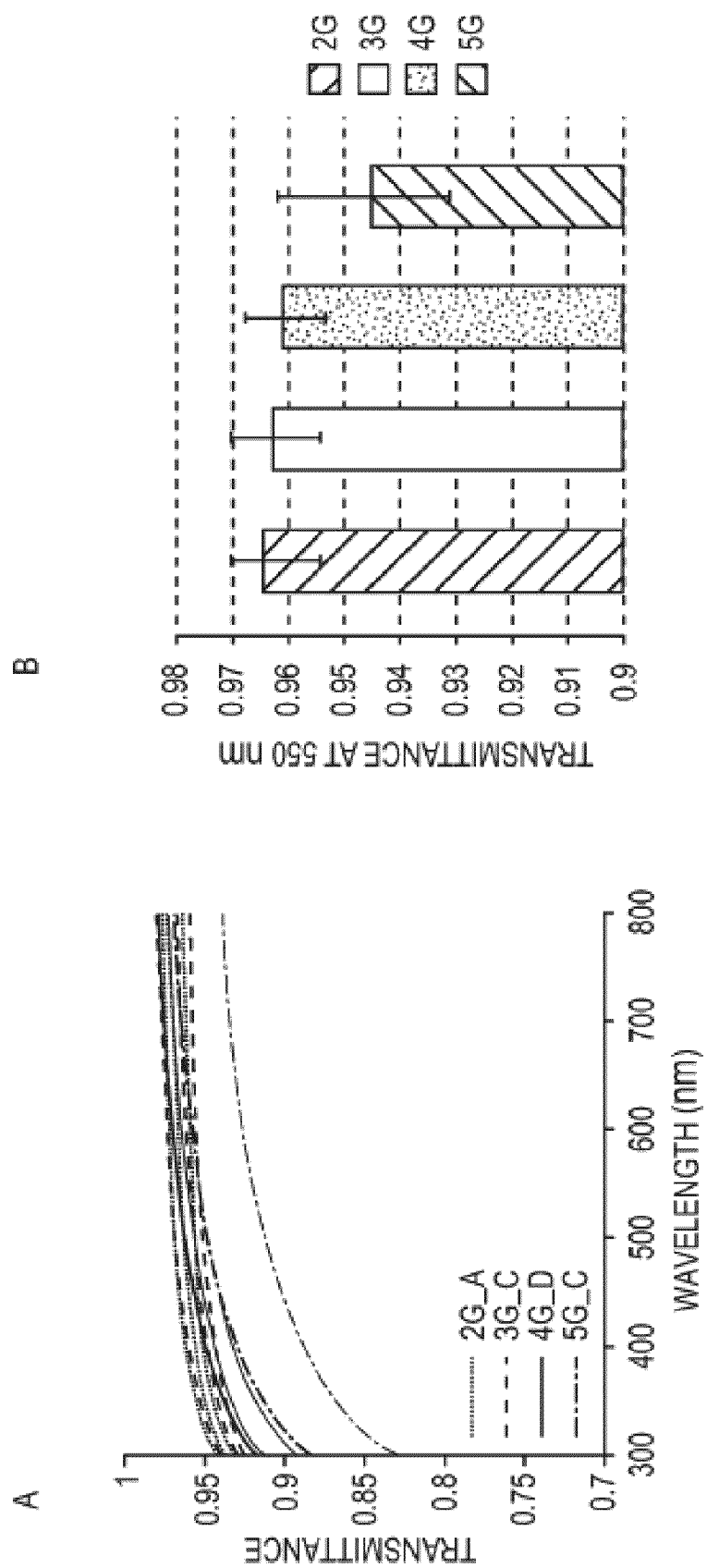

FIGS. 7A-B show the effects of cellulose concentration of the cellulose hydrogels on transparency.

Figure 8:
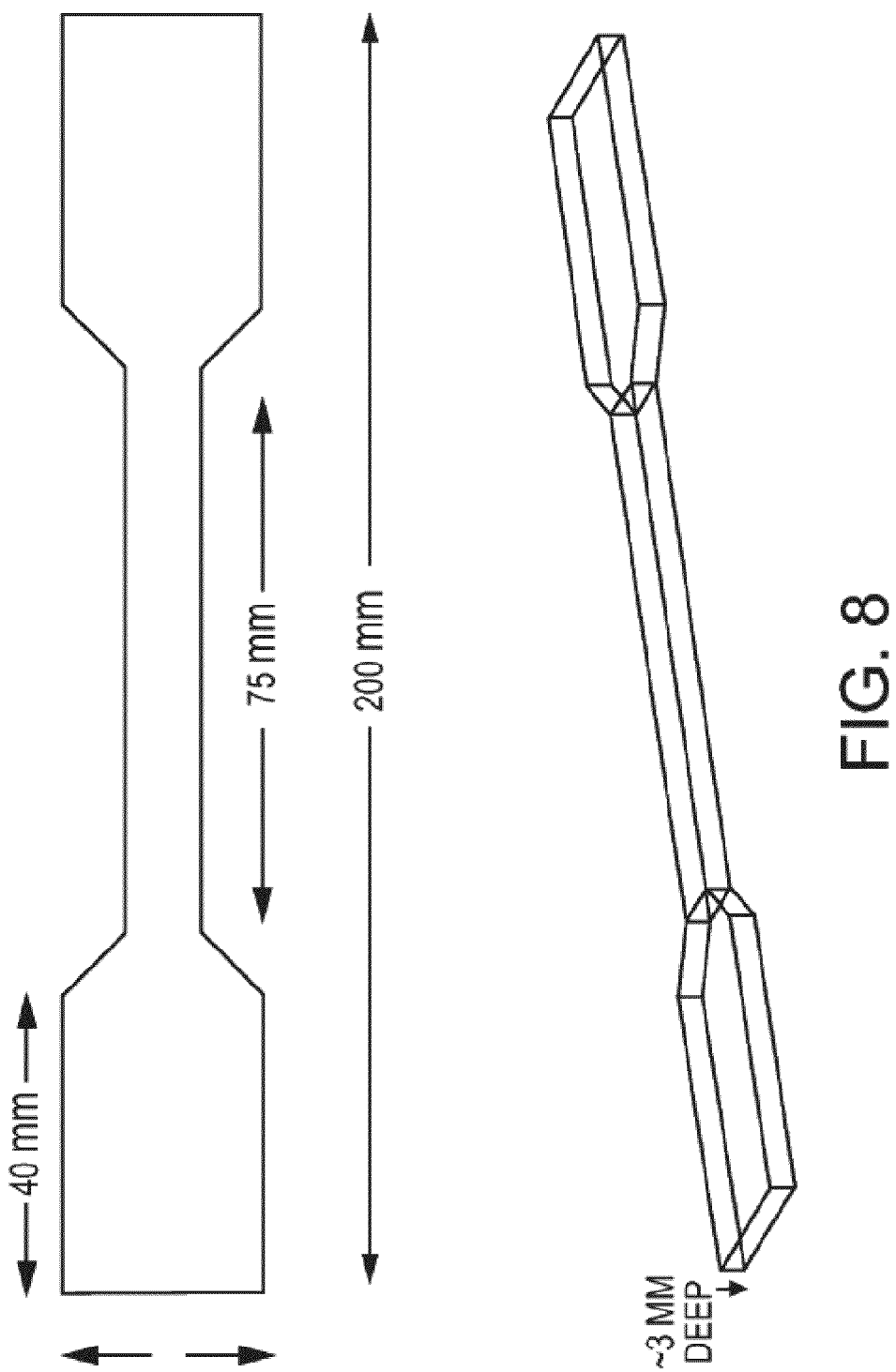

FIG. 8 shows dogbone mold dimensions used for tensile testing wet gels.

Figures 9A, 9B:
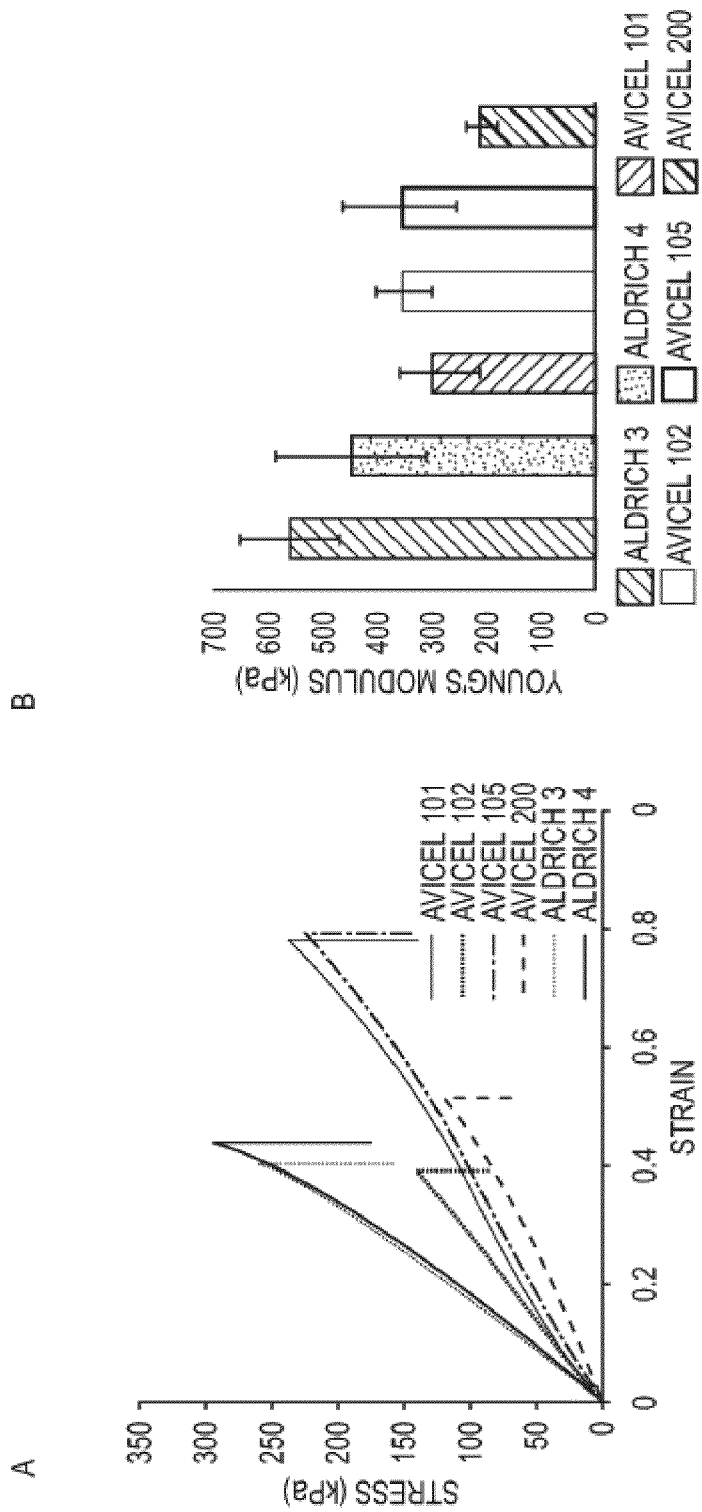

FIGS. 9A-B show tensile behavior and Young's Modulus data for wet cellulose hydrogels.

FIG. 10 shows tensile behavior for wet bacterial cellulose hydrogels (500 mg in 50 mL LiCl/DMAc).

Figure 11B:
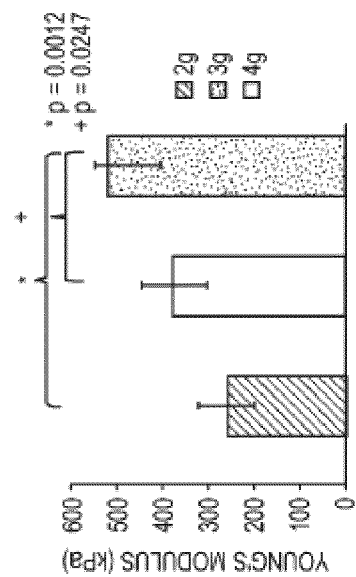
Figure 11A:
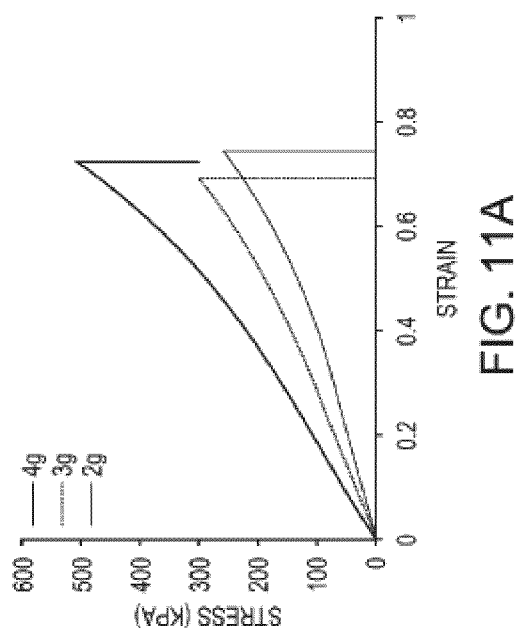

FIGS. 11A-C show tensile properties of wet hydrogels dependent on cellulose concentration.

Figure 12:
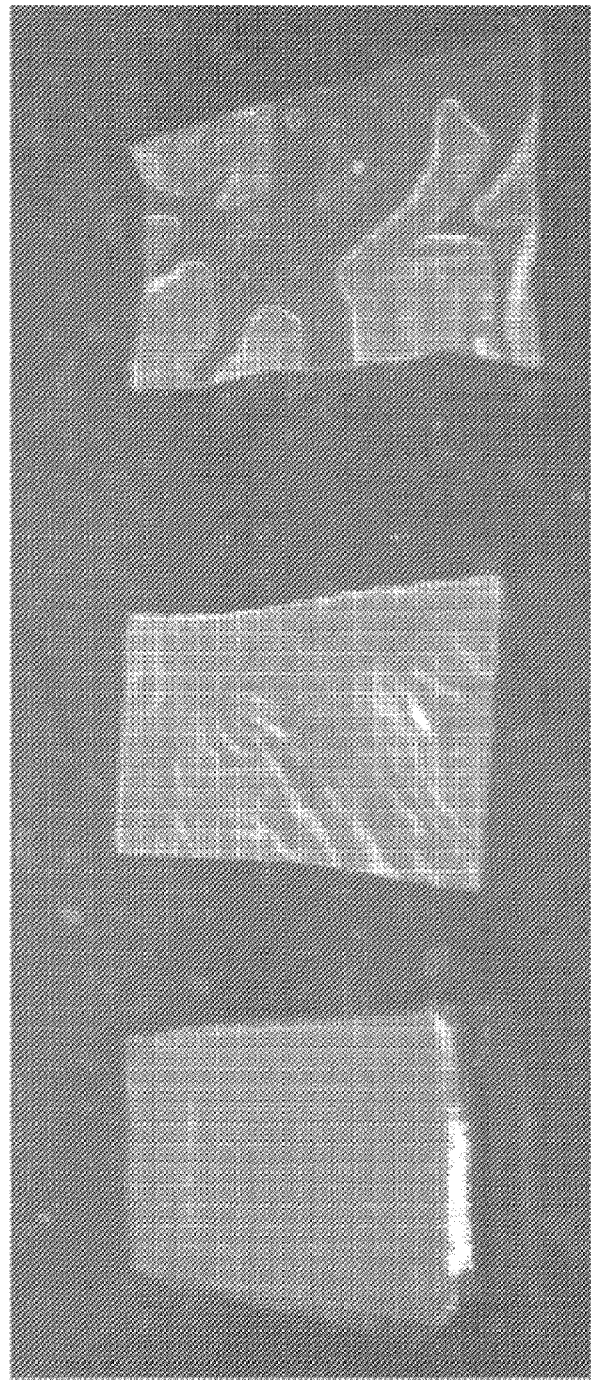

FIG. 12 shows images of wet, dry, and re-wet gels.

Figure 13:
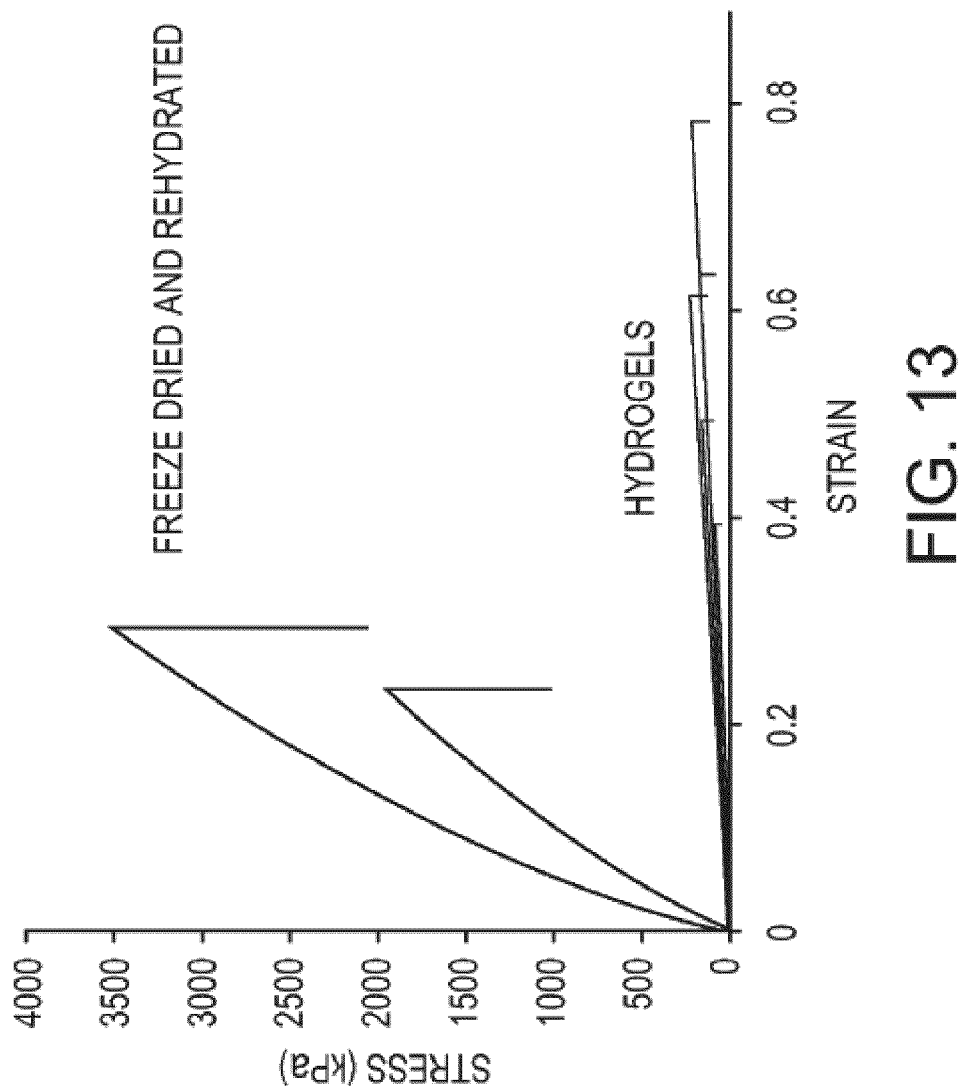

FIG. 13 shows results demonstrating increased tensile strength of cellulose hydrogels after a drying and rehydration step (re-wet cellulose hydrogels).

Figure 14A:
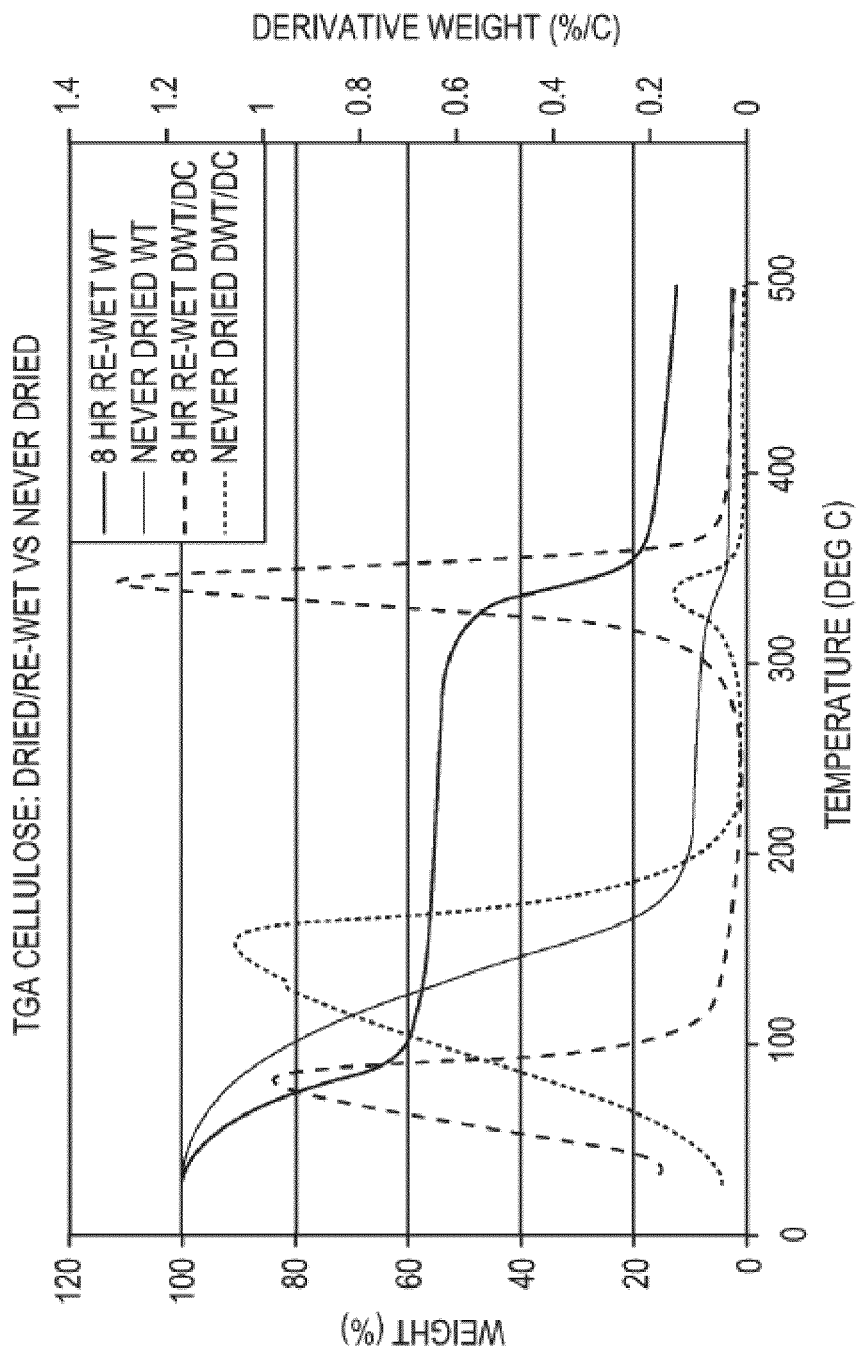
Figure 14B:
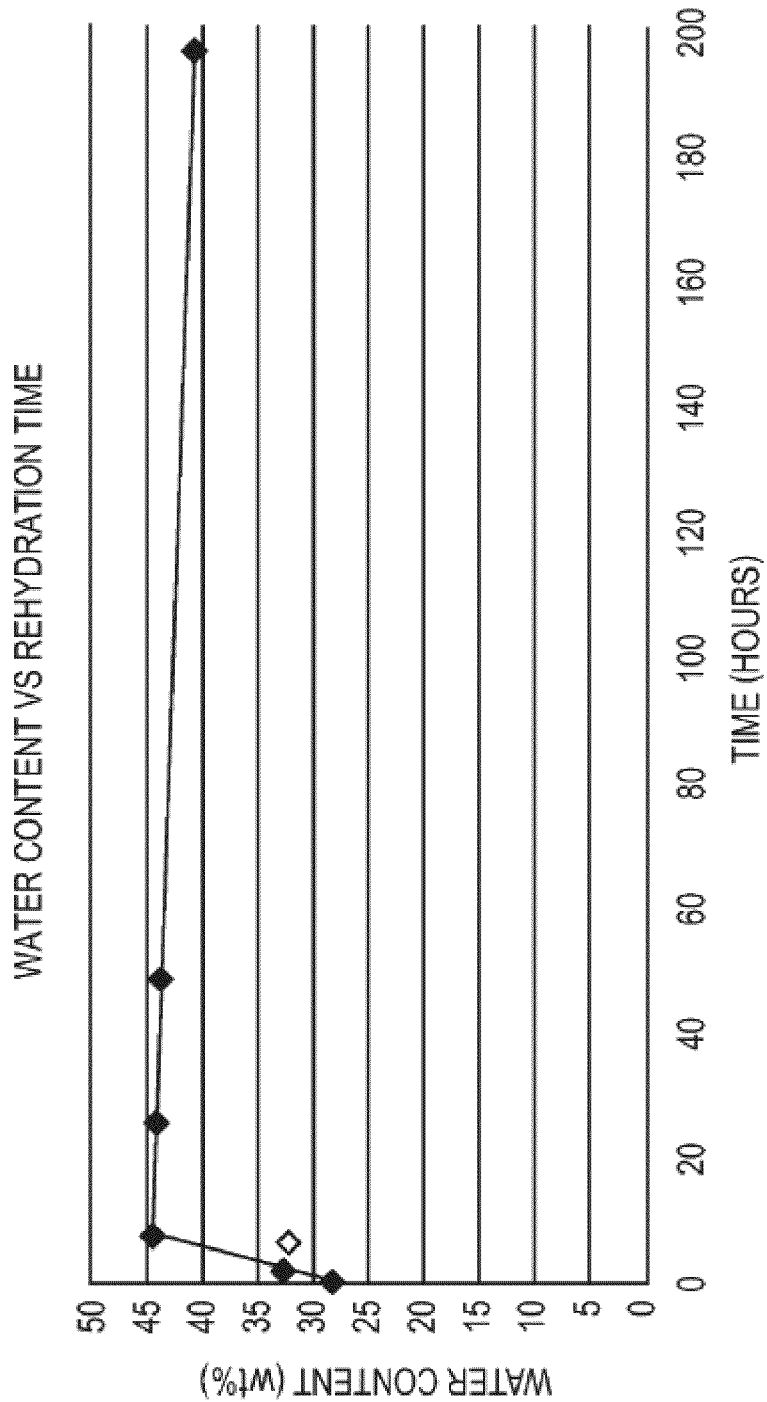

FIG. 14A shows TGA analysis of dried, re-wet and wet (never dried) hydrogels. FIG. 14B shows water content of rehydrated gels as a function of rehydration time.

Figures 15A, 15B:
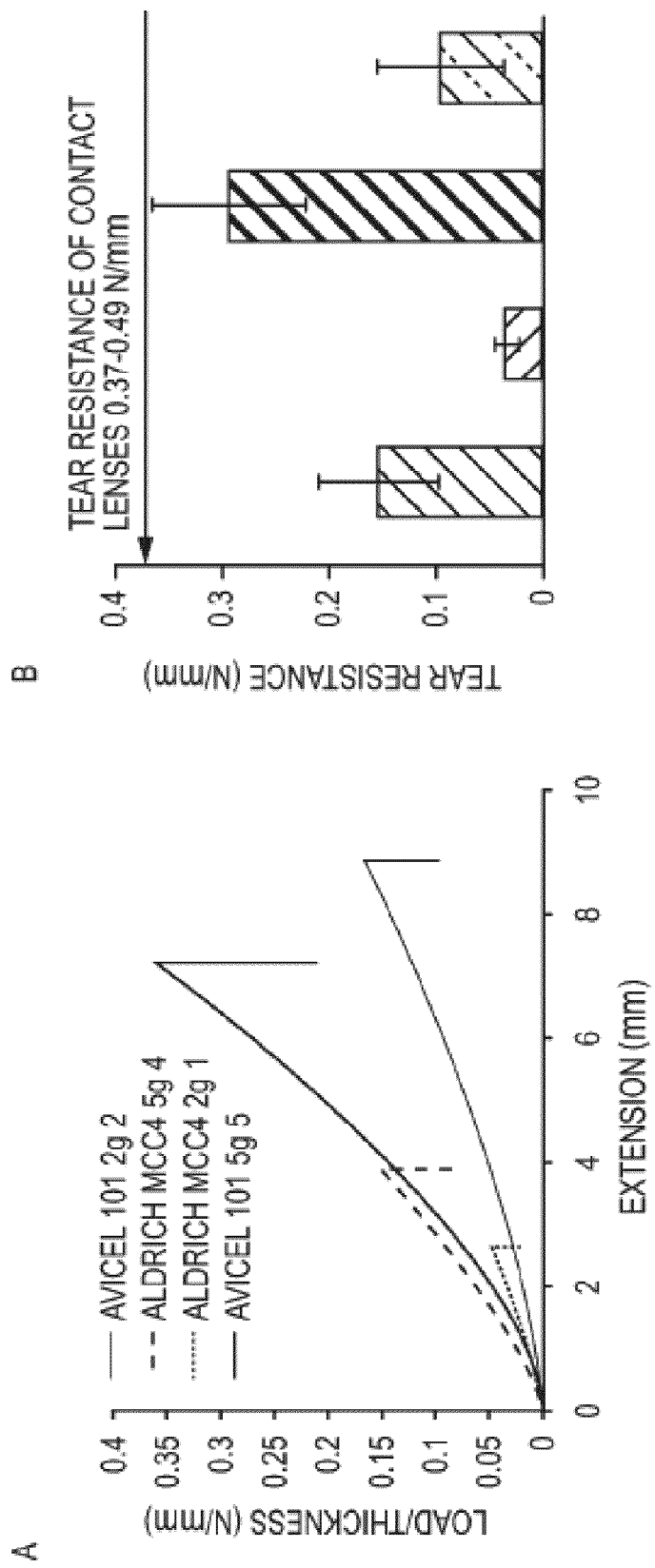

FIGS. 15A-B show tear resistance data for wet cellulose hydrogels.

Figure 16:
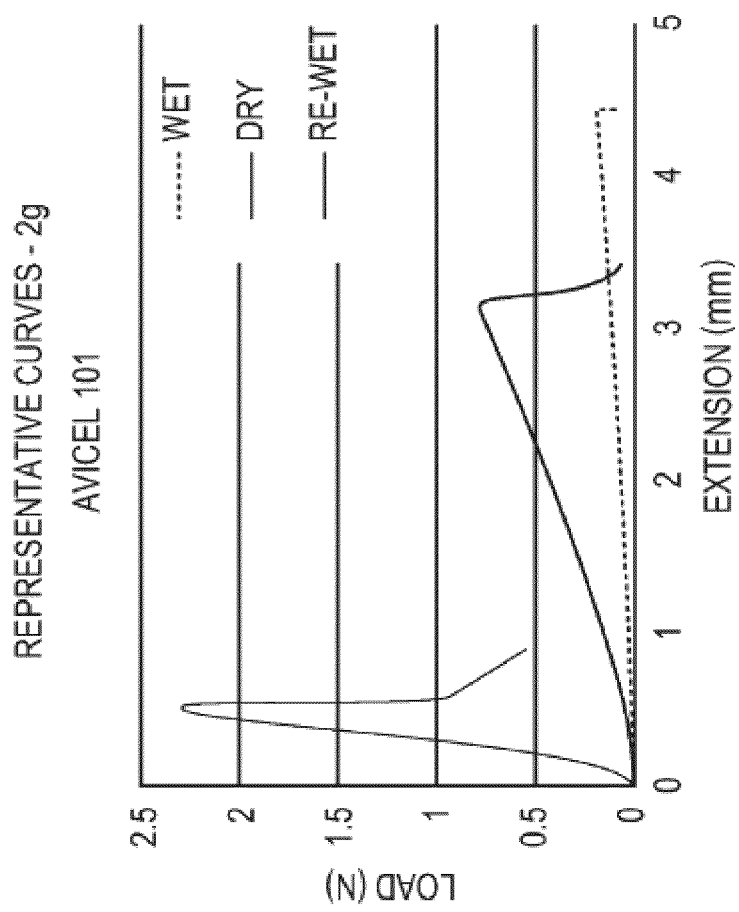

FIG. 16 shows tear resistance data comparisons for wet, dry and re-wet cellulose hydrogels (Avicel 101; made from 2 grams of cellulose in 100 ml of solvent).

Figure 17:
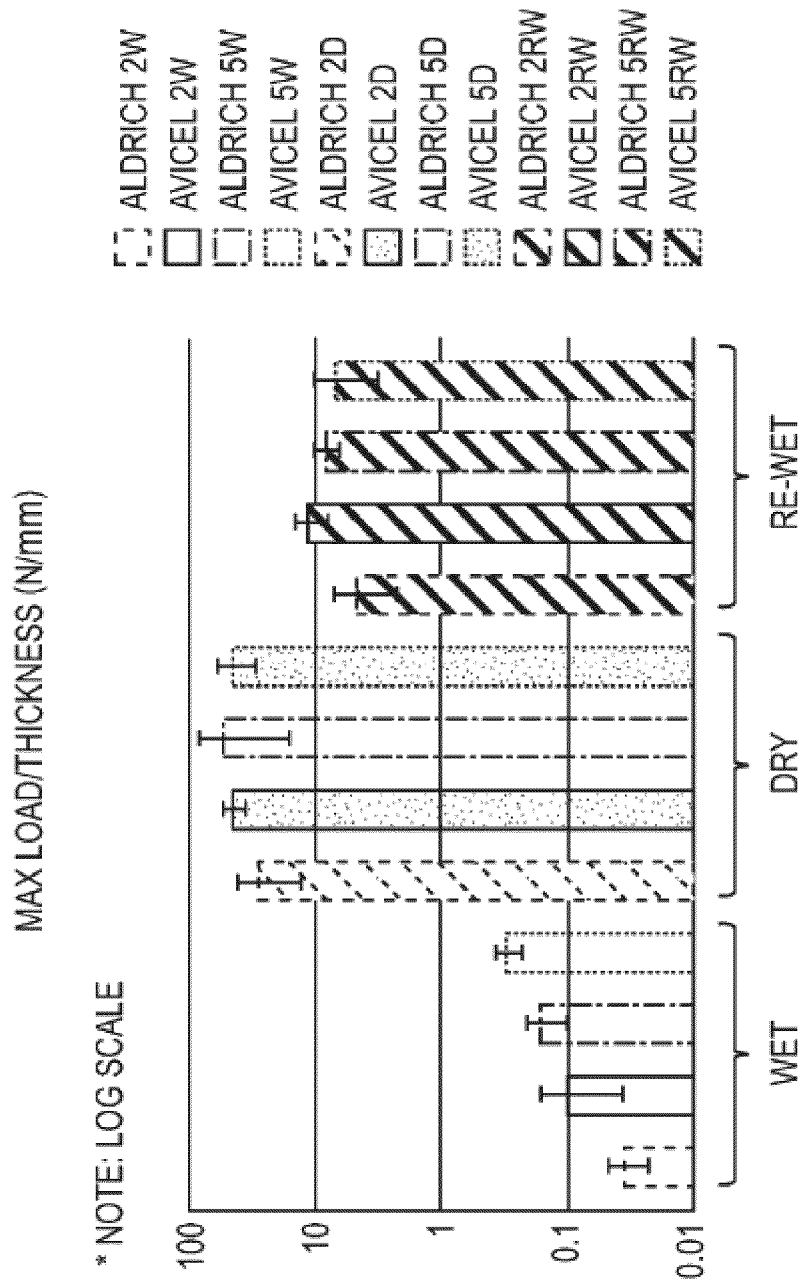

FIG. 17 shows tear strength of wet (w), dry (d) and re-wet (rw) cellulose hydrogels at 2 and 5 gram concentrations (Avicel 101 and Aldrich 4).

Figure 18:
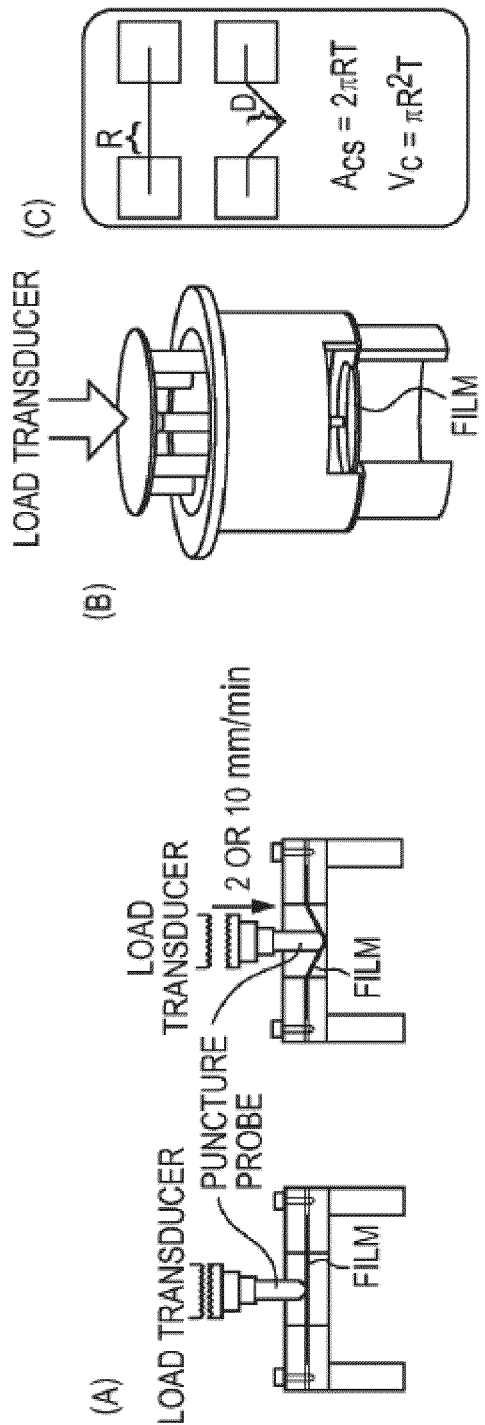
Figures 19A, 19B, 19C, 19D:
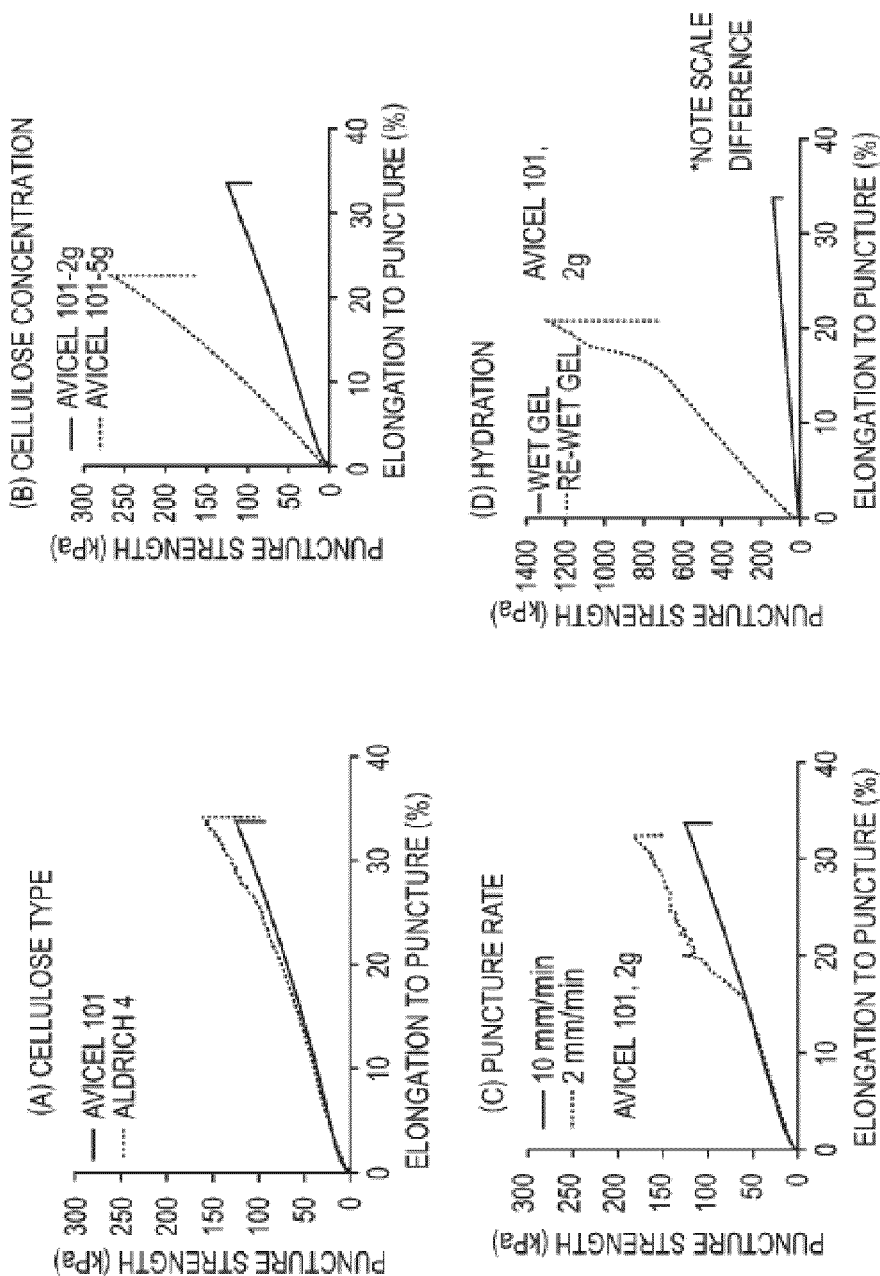

FIG. 18 (A) shows a schematic for testing puncture resistance (B) a puncture test fixture for testing cellulose hydrogels using the setup of (A), and (C) gel dimensions and variables used for calculations. (A) is adapted from Radebaugh et al., Int J Pharmaceutics 45, 1988, p 39-46.

FIGS. 19A-D show a summary of puncture test results for cellulose hydrogels.

Figure 20:
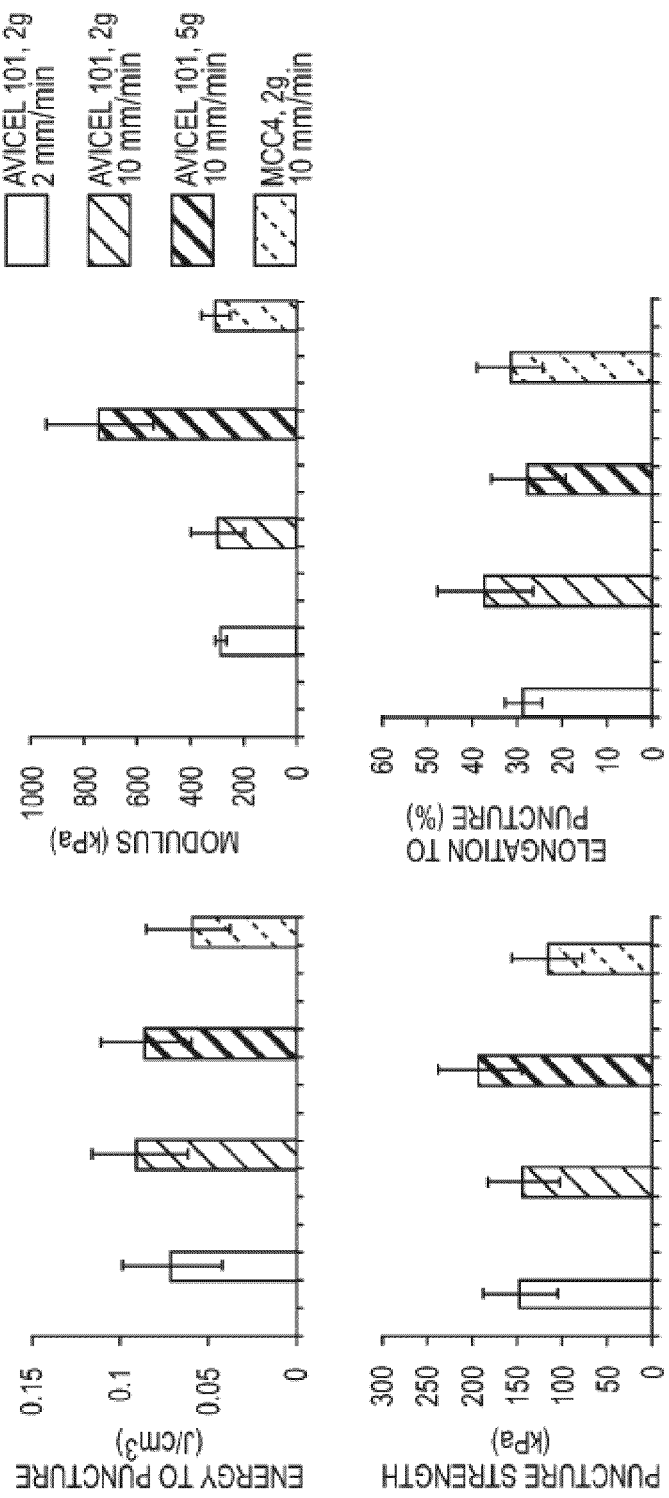

FIG. 20 shows a summary of puncture test results.

Figures 21A, 21B:
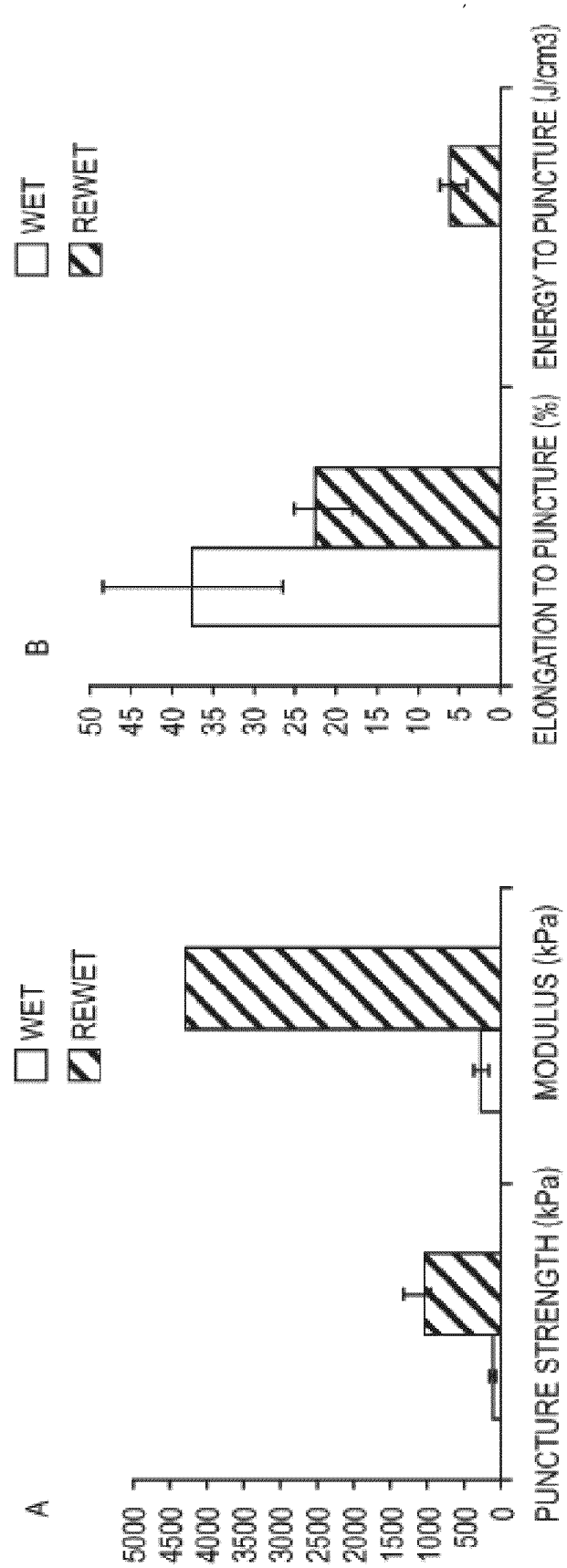

FIGS. 21A-B show puncture stiffness results for wet and re-wet Avicel 101 (2 grams of cellulose in 100 ml of solvent) hydrogels.

Figure 22:
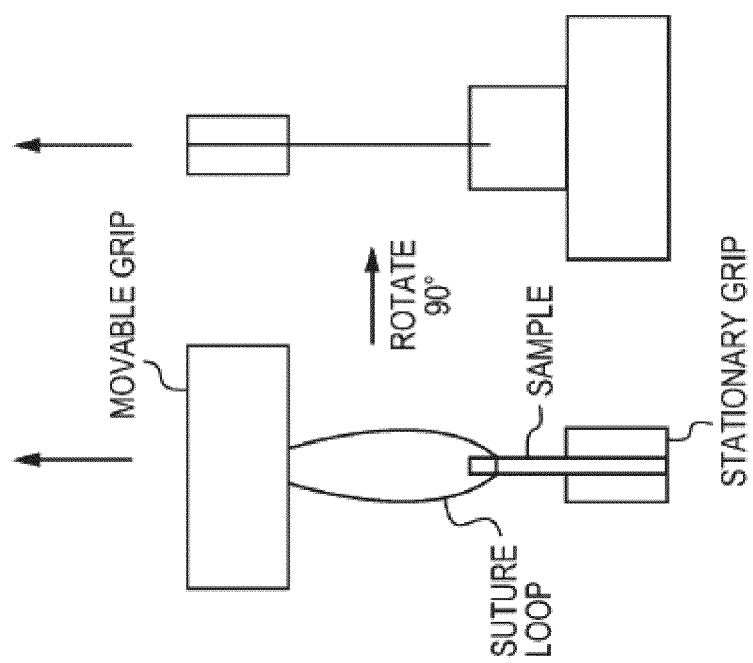

FIG. 22 shows a schematic diagram of sample set up for suture retention strength tests.

Figure 23:
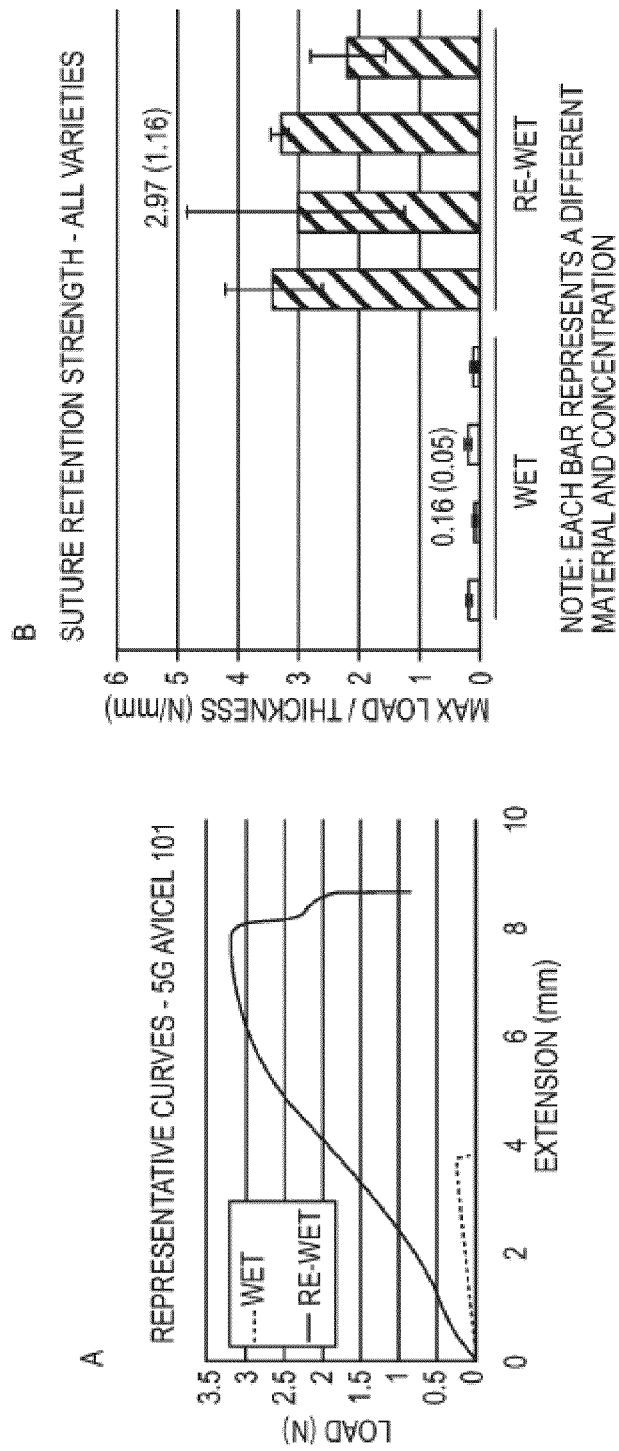

FIG. 23 shows suture retention strength data for wet and re-wet hydrogels. (A) shows a plot of load (N) versus extension (mm) for a wet and re-wet Avicel 101 hydrogel (5 grams of cellulose per 100 ml of solvent). (B) shows a graph of suture retention strength for various wet and re-wet hydrogels.

Figure 24:
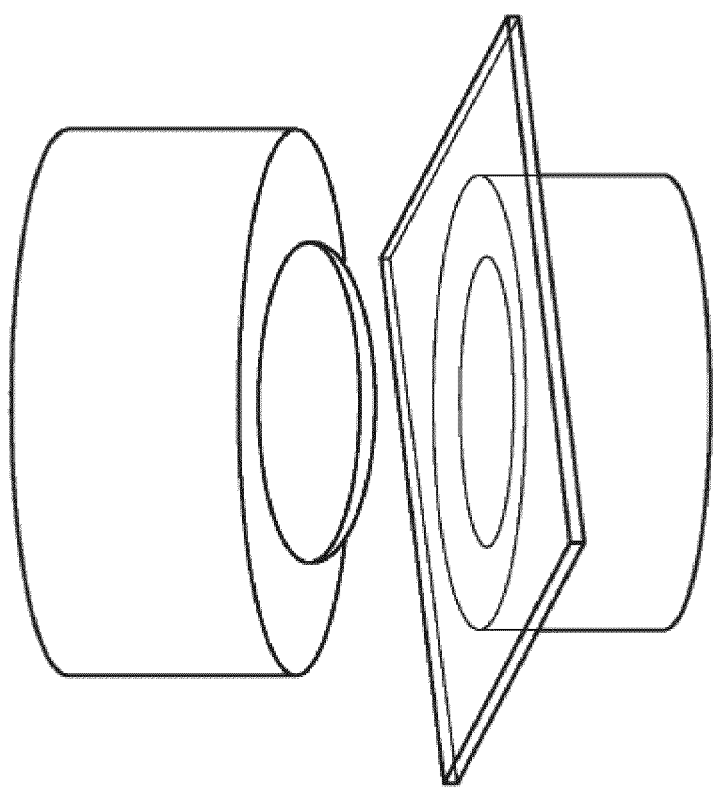

FIG. 24 shows a method of making a molded contact lens from a cellulose sheet.

Figure 25A:
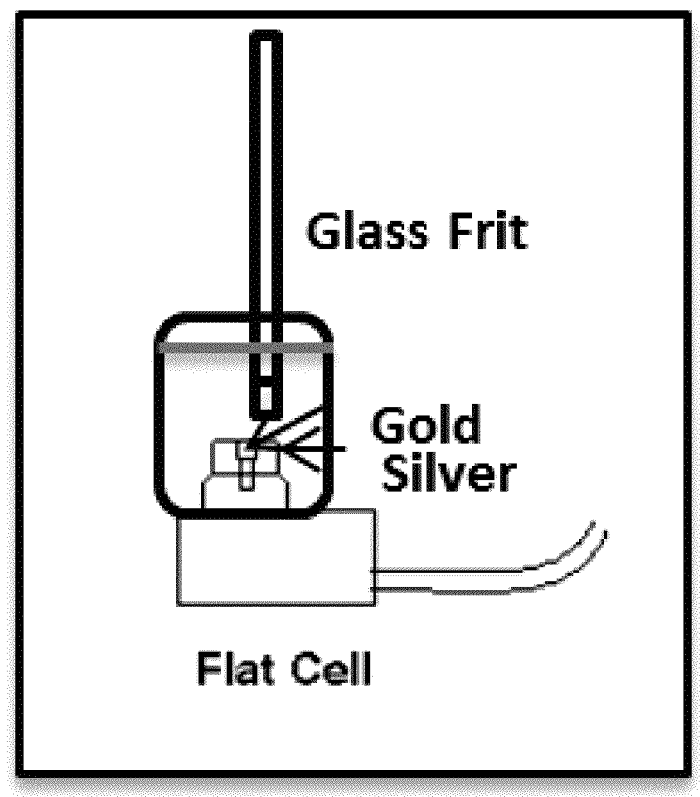

FIG. 25A illustrates a diagram of the polarographic cell used for the measurement of oxygen permeability of the hydrogels.

Figure 25B:
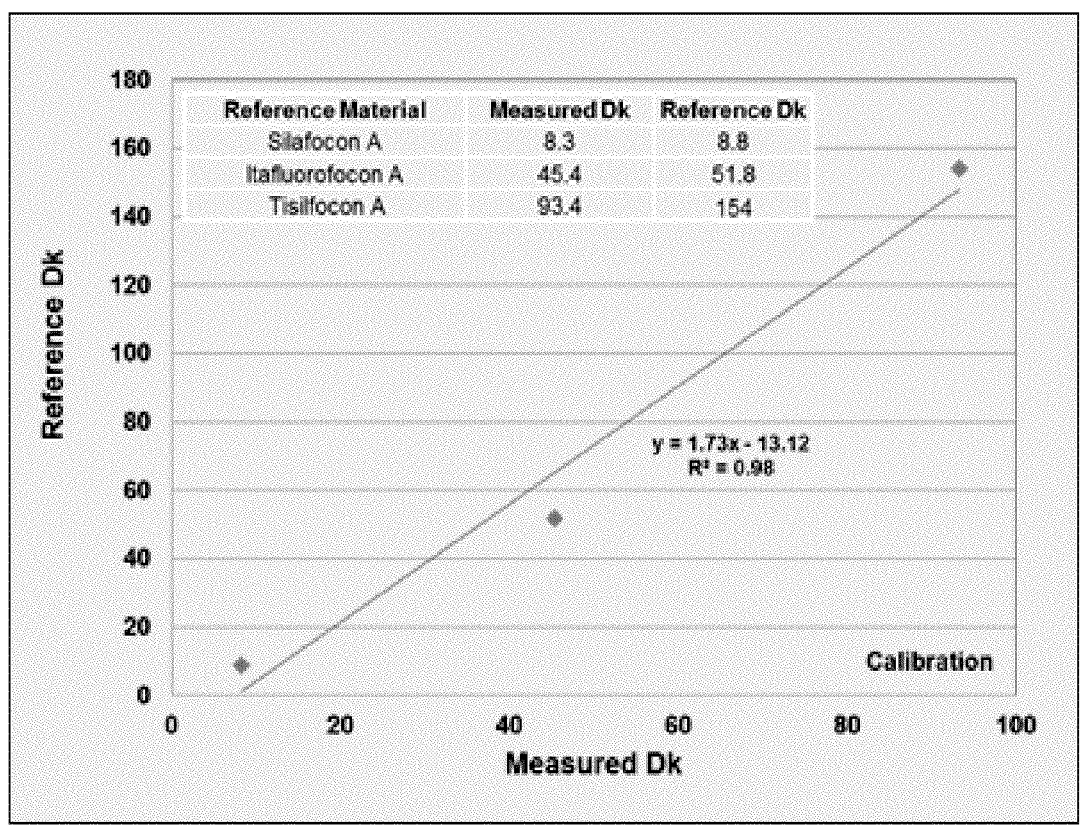

FIG. 25B shows the calibration curve from which permeability of samples (e.g., hydrogels according to certain embodiments of the present invention) was calculated.

Figures 25C, 26A, 26B, 26C, 26D, 26E, 26F, 26G, 26H:
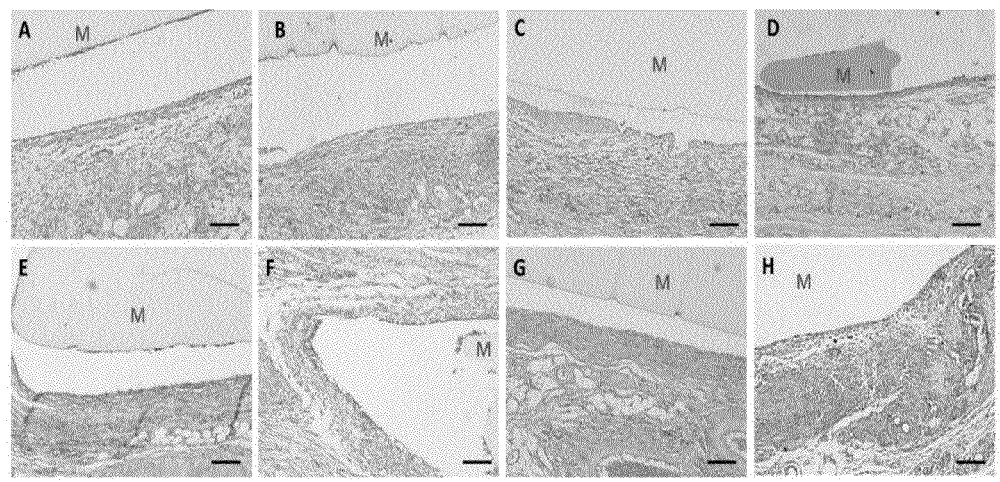

FIG. 25C shows that the average oxygen permeability for hydrogels, according to certain embodiments of the present invention, ranged from 60 to 94 Dk.

FIGS. 26A-26H shows H&E staining images of cellulose hydrogels after 2 days and after 7 days for hydrogel implants and surrounding tissues with Avicel 101 (26A and 26E), bacterial cellulose (26B and 26F), and MCC4 (26C and 26G), and PMMA (26D and 26H).

Figure 27A:
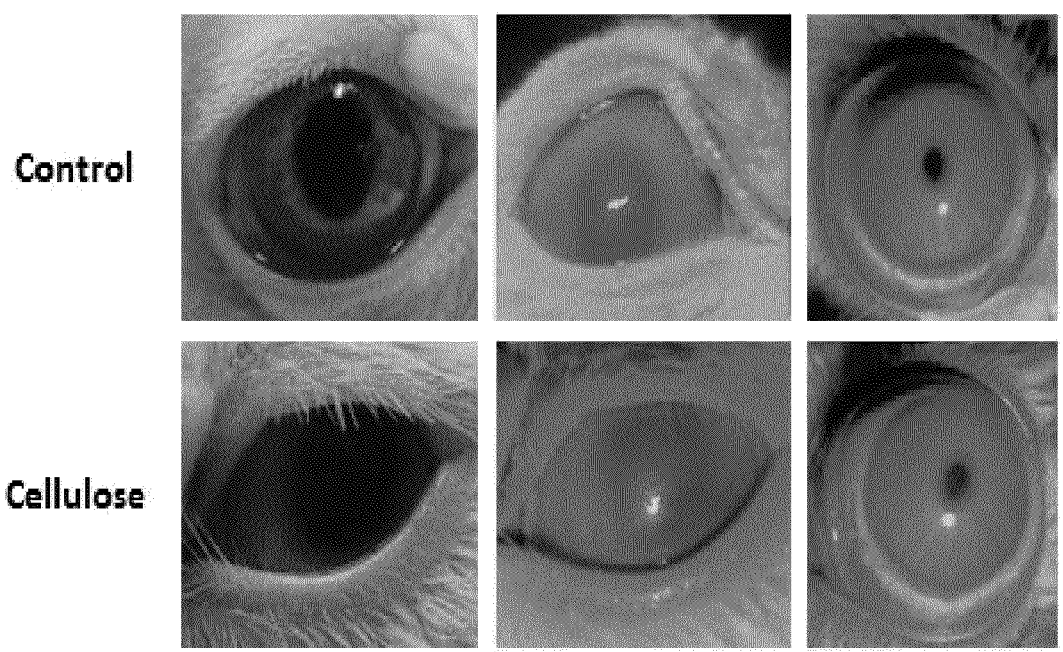

FIG. 27A shows the lens fit (far left) and abrasion (far right) after circular rubbing 50 times.

Figure 27B:
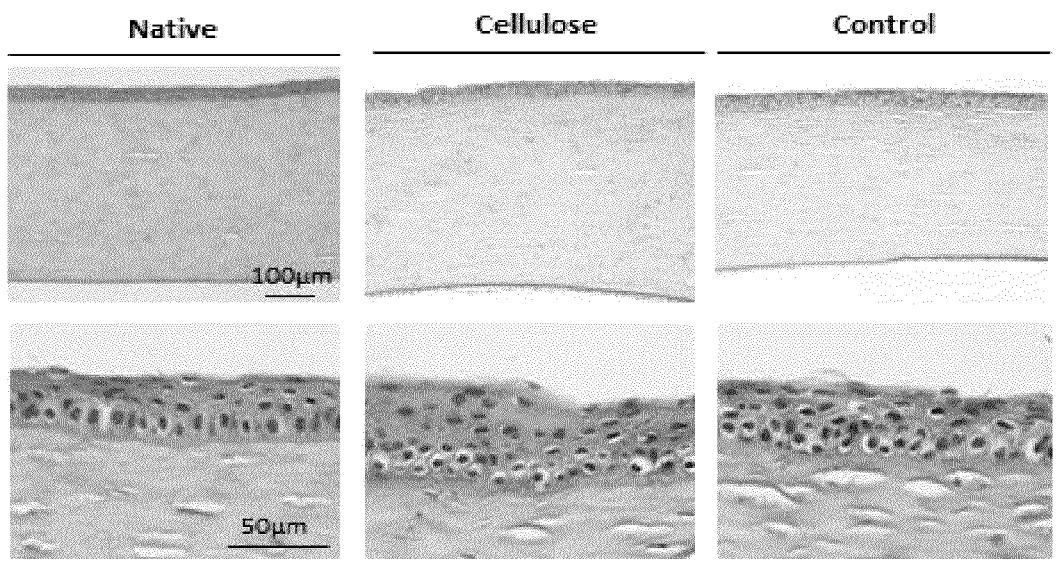

FIG. 27B shows the histology after 21 days of wear with a minimum of 7 hours per day of wear.

DETAILED DESCRIPTION

The present invention now will be described more fully hereinafter with reference to the accompanying drawings, in which some, but not all embodiments of the inventions are shown. Indeed, this invention may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

For the purposes of promoting an understanding of the principles of the invention, reference will now be made to certain embodiments and specific language will be used to describe the same. It will nevertheless be understood that no limitation of the scope of the invention is thereby intended, and alterations and modifications in the illustrated device, and further applications of the principles of the invention as illustrated therein are herein contemplated as would normally occur to one skilled in the art to which the invention relates.

Unless defined otherwise, all technical and scientific terms used herein have the same meaning as commonly understood by one of ordinary skill in the art to which this invention pertains.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the term "cellulose hydrogel" encompasses a polymeric material generally of the formula $(C_6H_{10}O_5)_n$ which exhibits the ability to swell in water or aqueous solution without dissolution and to retain a significant portion of water or aqueous solution within its structure. In some embodiments, the cellulose can be modified. In some embodiments, the cellulose includes modified forms such as cellulose nitrate, acetate or carboxymethylcellulose, methyl-cellulose, hydroxyethylcellulose, hydroxypropylcellulose, hydroxypropylmethylcellulose and combinations thereof. In some embodiments, the cellulose is modified to create added functional groups.

The term "biocompatible," as used herein, refers to an ability to be incorporated into a biological system, such as into an organ or tissue of an animal, without stimulating an adverse immune or inflammatory response.

As used herein, the term "about" refers to a ±10% variation from the nominal value. It is to be understood that such a variation is always included in any given value provided herein, whether or not it is specifically referred to.

In some embodiments, the present invention relates to improved cellulose-based hydrogels having a combination of desirable characteristics. Such desirable characteristics can include tensile strength, tear strength, suture retention strength, transparency, puncture resistance, oxygen permeability, strain, low cellulose content and high water content, and combinations thereof. In some embodiments of the invention, the cellulose hydrogels are "wet" and in some embodiments, the cellulose hydrogels are "re-wet." As used herein, "wet" cellulose hydrogels are gels that have not been subjected to a dehydration step, whereas "re-wet" cellulose hydrogels have been dehydrated, and subsequently rehydrated. Surprisingly, re-wet cellulose hydrogels exhibit significantly enhanced tensile properties as compared with wet cellulose hydrogels.

The cellulose hydrogels according to certain embodiments of the present invention can have multiple uses and applications. For example, the hydrogels are useful in ophthalmic applications, such as contact lenses for vision correction, corneal onlays, corneal inlays, artificial lenses, corneal bandages, and artificial corneas, as well as for wound dressing applications.

The cellulose that is used to make the hydrogel can, according to certain embodiments, come from any source and can include commercial and non-commercial sources of cellulose. Cellulose is prevalent in plants and some microbes, and thus, in accordance with the invention, cellulose can be used from any plant source or microbial or bacterial source that produces it. In some embodiments, the cellulose that is used is not from a microbial/bacterial source.

In some embodiments, the cellulose can be from a microbial/bacterial source. The cellulose-producing microorganism can be of the genus *Gluconacetobacter, Agrobacterium, Rhizobium, Pseudomonas* or *Alcaligenes*. In some embodiments, the source is from the species *Gluconacetobacter xylinus* or *Gluconacetobacter pasteurianus*. Bacterial cellulose is generally available commercially under the trade names XCELL, BIOFILL, BIOPROCESS and DERMAFILL. Microorganisms or organisms or cells that have been transformed (permanently or transiently) with one or more genes capable or required for manufacturing cellulose and strains or sub-strains related to or derived therefrom can also provide sources of cellulose. In some embodiments, the bacterial cellulose is from a commercial source (for example, from Xylos Corporation, Langhorne, Pa.).

Exemplary plant sources of cellulose include wood pulp, cotton pulp, flax, hemp, jute, and straw, to name a few. In some embodiments, the cellulose is from a source selected from the group consisting of wood pulp, cotton pulp, and combinations thereof. In some embodiments, the source of cellulose is microcrystalline cellulose. Commercial sources of cellulose include those that are sold under the trade name AVICEL, such as AVICEL PH 101, AVICEL PH 102, AVICEL PH 103, AVICEL PH 105, AVICEL PH 112, AVICEL PH 113, AVICEL PH 200, AVICEL PH 301, AVICEL PH 302, and AVICEL PH 200LM. The cellulose hydrogel can be derived from one or more sources of cellulose. In some embodiments, a combination of microcrystalline cellulose from a commercial source is combined with cellulose from a microbial/bacterial source, such as *Gluconacetobacter xylinus*.

In some embodiments, the cellulose (starting material, not gel) has a cellulose density of between about 0.10-0.60 g/cm$^{-1}$. In some embodiments, the cellulose density is between about 0.20-0.40 g/cm$^3$. In some embodiments, the cellulose has a moisture content of between about 2-6%.

In some embodiments the cellulose (starting material, not gel) has a particle size ranging from about 25 μm to about 500 μm, from about 35 μm to about 400 μm, or from about 50 min to about 250 μm. In some embodiments the particle size is about 25 μm, about 35 μm, about 50 μm, about 60 μm, about 75 μm, about 90 μm, about 100 μm, about 125 Gun, about 150 μm, about 175 μm, about 200 μm, about 250 μm, about 300 μm, about 350 μm or about 400 μm.

In some embodiments, the invention provides a re-wet cellulose hydrogel wherein the hydrogel has one or more (or all) of the following properties: a cellulose content of from about 40% to about 65% by weight; a tensile strength in the range of from about 1000 kPa to about 5000 kPa; a tear strength of from about 3.0 N/mm to about 12 N/mm; a strain to failure of from about 20% to about 40%; a suture retention strength of from about 1.0 N/mm to about 7.0 N/mm; a transparency that exceeds 85% at 550 nm; Young's modulus of from about 4000 kPa to about 15000 kPa; and a puncture resistance of from about 3 MPa to about 5 MPa.

In one embodiment, the invention provides a re-wet cellulose hydrogel wherein the hydrogel has a tensile strength of at least about 1000 kPa, a cellulose concentration of about 40% to about 65% by weight, and a transparency that exceeds 85% at 550 nm.

In some embodiments, the invention provides a wet cellulose hydrogel wherein the hydrogel has one or more (or all) of the following properties: a cellulose content of from about 1% to about 10% by weight; a tensile strength in the range of from about 50 kPa to about 4000 kPa; a tear strength of from about 0.10 N/mm to about 3 N/mm; a transparency that exceeds 85% at 550 nm; a strain to failure of from about 40% to about 160%; a suture retention strength of from about 0.1 N/mm to about 0.21 N/mm; Young's modulus of from about 100 kPa to about 1600 kPa; and a puncture resistance of from about 50 kPa to about 300 kPa.

In accordance with the invention, the tensile strength of the cellulose hydrogel can be found by performing a tensile test and recording the force and displacement. These are then converted to stress (using cross sectional area) and strain; the highest point of the stress-strain curve is the "ultimate tensile strength." In some embodiments, tensile strength can be characterized using a 500N capacity tabletop mechanical testing system (#5942R4910, Instron) with a 5N maximum static load cell (#102608, Instron). Pneumatic side action grips can be used to secure the samples (#2712-019, Instron). In some embodiments, a constant extension rate (for example, of about 2 mm/min) until failure can be applied and the tensile strength is calculated from the stress vs. strain data plots.

In some embodiments, the wet cellulose hydrogel has a tensile strength in the range of about 50 kPa to about 4000 kPa. In some embodiments, the tensile strength is from about 75 kPa to about 500 kPa, from about 100 kPa to about 400 kPa, from about 150 kPa to about 350 kPa, or from about 200 kPa to about 300 kPa. In some embodiments, the tensile strength is at least about 50 kPa, at least about 75 kPa, at least about 100 kPa, at least about 150 kPa, at least about 200 kPa, at least about 250 kPa, at least about 300 kPa, at least about 350 kPa, at least about 400 kPa, at least about 450 kPa, at least about 500 kPa, at least about 550 kPa or at least about 600 kPa.

In accordance with certain embodiments, the wet cellulose hydrogel may have a tensile strength comprising from at least any of the following: 50, 250, 500, 600, 625, 650, 700, 800, 900, 1000, 1250, and 1500 kPa and/or at most about any of the following 4000, 3500, 3000, 2500, 2000, and 1500 kPa (e.g., 625–3500 kPa, 1000–1500 kPa, etc.).

In some embodiments, the re-wet cellulose hydrogel has a tensile strength in the range of from about 1000 kPa to about 5000 kPa. In some embodiments, the tensile strength is from about 1250 kPa to about 4500 kPa. In some embodiments, the tensile strength is from about 1500 kPa to about 3500 kPa, from about 1750 kPa to about 3500 kPa, from about 2000 kPa to about 3500 kPa, from about 2000 kPa to about 3000 kPa, from about 2250 kPa to about 2750 kPa, and from about 2250 kPa to about 2500 kPa. In some embodiments, the tensile strength is at least about 1000 kPa, at least about 1100 kPa, at least about 1200 kPa, at least about 1300 kPa, at least about 1400 kPa, at least about 1500 kPa, at least about 1600 kPa, at least about 1700 kPa, at least about 1800 kPa, at least about 1900 kPa, at least about 2000 kPa, at least about 2100 kPa, at least about 2200 kPa, at least about 2300 kPa, at least about 2400 kPa, at least about 2500 kPa, at least about 2600 kPa, at least about 2700 kPa, at least about 2800 kPa, at least about 2900 kPa, at least about 3000 kPa, at least about 3100 kPa, at least about 3200 kPa, at least about 3300 kPa, at least about 3400 kPa, at least about 3500 kPa, at least about 3600 kPa, at least about 3700 kPa, at least about 3800 kPa, at least about 3900 kPa, at least about 4000 kPa, at least about 4100 kPa, at least about 4200 kPa, at least about 4300 kPa, at least about 4400 kPa, at least about 4500 kPa, at least about 4600 kPa, at least about 4700 kPa, at least about 4800 kPa, at least about 4900 kPa or at least about 5000 kPa.

In some embodiments of the invention, the tear strength property of the cellulose hydrogel can be tested using a 500N capacity tabletop mechanical testing system (#5942R4910, Instron) with a 5N maximum static load cell (#102608, Instron). Pneumatic side action grips can be used to secure the samples (#2712-019, Instron). Samples can be tested with a constant extension rate (for example, of about 2 mm/min) until failure. In accordance with the invention, tear strength is calculated as the force at failure divided by the average thickness (N/mm).

In some embodiments, the wet cellulose hydrogel has a tear strength of from about 0.10 N/mm to about 3 N/mm. In some embodiments, the tear strength is from about 0.20 N/mm to about 0.40 N/mm, or from about 0.25 N/mm to about 0.35 N/mm. In some embodiments, the tear strength is at least about 0.10 N/mm, at least about 0.15 N/mm, at least about 0.20 N/mm, at least about 0.25 N/mm, at least about 0.30 N/mm, at least about 0.35 N/mm, at least about 0.40 N/mm, at least about 0.45 N/mm, at least about 0.55 N/mm or at least about 0.60 N/mm.

In accordance with certain embodiments, the wet cellulose hydrogel may have a tear strength comprising from at least any of the following: 0.1, 0.3, 0.5, 0.7, 0.8, 0.9, 1.0, 1.25 and 1.5 N/mm and/or at most about any of the following 3, 2.5, 2.0, and 1.5 N/mm (e.g., 0.7-3 N/mm, 1.5-3 N/mm, etc.).

In some embodiments, the re-wet cellulose hydrogel has a tear strength of from about 3.0 N/mm to about 12 N/mm. In some embodiments, the tear strength is from about 5.0 N/mm to about 8.0 N/mm, from about 6.0 N/mm to about 7.5 N/mm, from about 6.3 N/mm to about 7.3 N/mm or from about 6.5 N/mm to about 7.0 N/mm. In some embodiments, the tear strength is at least about 4.0 N/mm, at least about 4.5 N/mm, at least about 5.0 N/mm, at least about 5.5 N/mm, at least about 6.0 N/mm, at least about 6.5 N/mm, at least about 7.0 N/mm, at least about 7.5 N/mm, at least about 8.0 N/mm, at least about 8.5 N/mm or at least about 9.0 N/mm.

In some embodiments, strain to failure ranges from 40-160% for wet cellulose hydrogels. In some embodiments, the strain to failure ranges from about 40% to about 80%, from about 50% to about 70%, from about 50 to about 60%, from about 85% to about 160%, from about 100% to about 160%, from about 120% to about 150%.

In some embodiments, strain to failure ranges from about 20 to about 40% for re-wet cellulose hydrogels. In some embodiments, the strain to failure ranges from about 20% to about 30%, or from about 25% to about 30%.

In some embodiments of the invention, suture retention strength of cellulose hydrogels can be characterized as a measure of their feasibility for surgical implementation. In some embodiments, suture retention can be important for cellulose hydrogels to secure and maintain their position, for example, during surgery, healing and function. For example, in some embodiments, a surgeon must rely on the ability of the implantable material to not only accept suture without tearing during needle insertion, but also to retain the suture without tearing away from the sutured edge of the implant. To perform suture retention strength studies, cellulose hydrogel samples can be cut from cellulose sheets. For example, samples can be cut to be rectangles 2 cm×4 cm. The samples can be tested using a 500N capacity tabletop mechanical testing system (#5942R4910, Instron) with a 5N maximum static load cell (#102608, Instron). Pneumatic side action grips can be used to secure the samples (#2712-019, Instron). Before testing, the thickness of the sample can be measured at three points along one of the short edges (designated the top edge). The sample can then be secured in the stationary (bottom) pneumatic grip, with half of the sample inside of the grip, and a suture was threaded through the sample once in the center of the sample with a bite size of 2 mm from the top edge. For example, Ethicon Ethilon 10-0 ophthalmic sutures can be used (7756G and 7711G. Ethicon, Inc.). Both ends of the suture can be secured in the movable (top) pneumatic grip. See FIG. 22 for a diagram of the sample setup. Samples can be tested with a constant extension rate (for example, of 10 mm/min) until failure. The suture retention strength can be taken to be the force at failure divided by the average sample thickness (N/mm).

In some embodiments, the suture retention strength of wet cellulose hydrogels is from about 0.1 N/mm to about 0.30 N/mm. In some embodiments, the suture retention strength is from about 0.1 N/mm to about 0.23 N/mm, from about 0.1 N/mm to about 0.21 N/mm or from about 0.12 N/mm to about 0.18 N/mm. In some embodiments, the suture retention strength is at least about 0.1 N/mm, at least about 0.12 N/mm, at least about 0.15 N/mm, at least about 0.20 N/mm, at least about 0.25 N/mm, or at least about 0.30 N/mm.

In some embodiments, the suture retention strength of re-wet cellulose hydrogels is from about 1.0 N/mm to about 7.0 N/mm. In some embodiments, the suture retention strength is from about 2.5 N/mm to about 6.0 N/mm, from about 3.0 N/mm to about 5.0 N/mm. In some embodiments, the suture retention strength is at least about 2.0 N/mm, at least about 2.25 N/mm, at least about 2.5 N/mm, at least about 2.75 N/mm, at least about 3.0 N/mm, at least about 3.25 N/mm, at least about 3.5 N/mm, at least about 3.75 N/mm, at least about 4.0 N/mm, at least about 4.25 N/mm, at least about 4.5 N/mm, at least about 4.75 N/mm, at least about 5.0 N/mm, at least about 5.25 N/mm, at least about 5.5 N/mm, at least about 5.75 N/mm, at least about 6.0 N/mm, at least about 6.25 N/mm, at least about 6.5 N/mm, at least about 6.75 N/mm or at least about 7.0 N/mm.

In some embodiments, the transmittance of the cellulose hydrogel can be measured in the range of wavelengths from 250 to 800 nm using, for example, a Perkin-Elmer Lambda 9500 series UV-visible spectrophotometer. In some embodiments, transmittance at 550 nm is measured. As transmittance is dependent upon thickness, the thickness of each sample can be measured with calipers prior to loading in the spectrophotometer. Transmittance values can be normalized to a thickness of 100 μm (or any thickness) according to $$F_{T-corr}(\lambda, t_2) = [e^{-\sigma_t(\lambda)t_1}]^{\frac{t_2}{t_1}} = [F_{T-corr}(\lambda, t_1)]^{\frac{t_2}{t_1}},$$

where $t_1$=actual specimen thickness, $t_2$=thickness to which transmittance measurements were normalized.

In some embodiments, the cellulose hydrogels (both wet and re-wet) have transparencies that exceed 85% at 550 nm. In some embodiments, the transparency exceeds 86% at 550 nm, 87% at 550 nm, 88% at 550 nm, 89% at 550 nm, 90% at 550 nm, 91% at 550 nm, 92% at 550 nm, 93% at 550 nm, 94% at 550 nm, 95% at 550 nm, 96% at 550 nm, 97% at 550 nm, 98% at 550 nm or 99% at 550 nm.

In some embodiments, Young's modulus of the cellulose hydrogel can be tested. Young's modulus generally can be determined based on the slope of the stress-strain curve, and is calculated as stress/strain in the linear elastic portion of the curve.

In some embodiments, Young's modulus of the wet cellulose hydrogel is from about 100 kPa to about 1600 kPa. In some embodiments, Young's modulus of the wet cellulose hydrogel is from about 150 kPa to about 500 kPa, from about 200 kPa to about 400 kPa or from about 250 kPa to about 350 kPa. In some embodiments, modulus is at least about 100 kPa, at least about 150 kPa, at least about 200 kPa, at least about 250 kPa, at least about 300 kPa, at least about 400 kPa, at least about 450 kPa, at least about 500 kPa, at least about 550 kPa, at least about 600 kPa, at least about 650 kPa or at least about 700 kPa.

In accordance with certain embodiments, the wet cellulose hydrogel may have a Young's modulus comprising from at least any of the following: 100, 200, 300, 400, 500, 600, 700, 750, 800, 900 and 1000 kPa and/or at most about any of the following 1600, 1500, 1400, 1300, 1200, 1100, 1000 and 900 kPa (e.g., 750–1600 kPa, 1000–1500 kPa, etc.).

In some embodiments, Young's modulus of the re-wet cellulose hydrogel is from about 4000 kPa to about 15000 kPa. In some embodiments, Young's modulus is from about 5000 kPa to about 13000 kPa, from about 6000 kPa to about 12000 kPa, from about 7000 kPa to about 12000 kPa, from about 8000 kPa to about 11000 kPa, or from about 9000 kPa to about 10000 kPa. In some embodiments, modulus is at least about 4000 kPa, at least about 4500 kPa, at least about 5000 kPa, at least about 5500 kPa, at least about 6000 kPa, at least about 6500 kPa, at least about 7000 kPa, at least about 7500 kPa, at least about 8000 kPa, at least about 8500 kPa, at least about 9000 kPa, at least about 9500 kPa, at least about 10000 kPa, at least about 10500 kPa, at least about 11000 kPa, at least about 11500 kPa, at least about 12000 kPa, at least about 12500 kPa, at least about 13000 kPa, at least about 13500 kPa, at least about 14000 kPa, at least about 14500 kPa or at least about 15000 kPa.

In some embodiments, puncture resistance can be characterized according to a slightly modified version of the method described by Radebaugh et al. (Radebaugh et al., *Int J Pharmaceutics* 45, 1988, p 39-46). A schematic of this setup can be seen in FIG. 18A and the fixture designed for this work is shown in FIG. 18B. Rather than fixing the hydrogel between two plates using screws, which can pinch or tear the gel, the hydrogels can be secured to the fixture with cyanoacrylate. In some embodiments, a hemispherical probe with a 2 mm diameter is lowered onto the gel at a rate of 2 or 10 mm/min. Elongation to puncture can be measured as $$\varepsilon_p(\%) = \frac{([R]^2 + [D]^2)^{1/2} - R}{R} \cdot 100,$$

puncture strength can be calculated as $$\sigma_{puncture}(kPa) = \frac{F}{A_{cs}},$$

and energy to puncture can be calculated as $$\Delta E_p(J/cm^3) = \frac{\int F \cdot D}{V_c},$$

where F=force and all other variables are defined in FIG. 18C.

In some embodiments, puncture resistance of the wet cellulose hydrogel is from about 50 kPa to about 300 kPa. In some embodiments, puncture resistance is from about 75 kPa to about 300 kPa. In some embodiments, puncture resistance is from about 100 kPa to about 300 kPa. In some embodiments, puncture resistance is from about 125 kPa to about 200 kPa. In some embodiments, puncture resistance is at least about 50 kPa, at least about 100 kPa, at least about 150 kPa, at least about 200 kPa, at least about 250 kPa, or at least about 300 kPa.

In some embodiments, puncture resistance of the re-wet cellulose hydrogel is from about 3 MPa to about 5 MPa. In some embodiments, puncture resistance is from about 3.5 MPa to about 5 MPa. In some embodiments, puncture resistance is from about 3.5 MPa to about 4.5 MPa. In some embodiments, puncture resistance is from about 4 MPa to about 4.5 MPa. In some embodiments, puncture resistance is at least about 3 MPa, at least about 3.5 MPa, at least about 4.0 MPa, at least about 4.5 MPa, or at least about 5.0 MPa.

In some embodiments, oxygen permeability of the cellulose hydrogel can be tested using a polarographic method. This method directly measures the number of oxygen molecules diffusing though the material by measuring an electric current generated by the reduction of oxygen at the cathode. In a single polarographic determination, four samples of the same material with different thicknesses can be used. This results in a linear relation between the inverse of oxygen transmissibility and the sample thickness. The sample can be placed onto the surface of the electrode (cell), fixed gently by pressing toward the electrode and retained with an o-ring. Then, a saline solution (e.g., 0.9% NaCl, pH 7.4) is poured into the reservoir on the material, and the system is ready for the measurement of the electric current. The system is held in a humidity chamber at 35° C. with high humidity (the polarographic cell and the saline solution were in the humidity chamber prior the measurement to achieve equilibrium conditions). The saline solution and the sample are saturated with atmospheric oxygen. To remove it, nitrogen gas is bubbled through a glass flit while monitoring current, until the current decreases to nearly zero. Once most of the oxygen is removed, air is bubbled into the solution, and the increase in electric current is observed as the oxygen molecules react with the cathode. The current is recorded until it reaches a stationary state.

In accordance with certain embodiments of the present invention, the wet cellulose hydrogel can comprise an oxygen permeability from about 55 to about 150 Dk. For instance, the wet cellulose hydrogel according to certain embodiments can comprise an oxygen permeability comprising from at least any of the following: 50, 55, 60, 70, 80, 90, and 100 Dk and/or at most about any of the following 160, 150, 140, 130, 120, 110, 100 and 90 Dk (e.g., 55-150 Dk, 80-120 Dk, etc.).

Thermal stability according to certain embodiments of the invention can comprise a desirable thermal stability for a wide variety of applications (e.g., end uses). For instance, cellulose hydrogels (e.g., both wet and re-wet) for various eye applications (e.g., corneal bandage applications) must have sufficient shelf life and be able to survive operational temperatures associated with, for example, an eye of a living mammal.

In accordance with certain embodiments of the present invention, the wet cellulose hydrogel can comprise a denaturation temperature of at least about 70° C. (e.g., the material does not denature at temperatures below about 70° C.). For instance, the wet cellulose hydrogel according to certain embodiments can comprise a denaturation temperature comprising from at least any of the following: 70, 80, 90, 100, 125, 150, 175, 200, 225, and 250° C. and/or at most about any of the following 330, 325, 320, 315, 310, 300, 275 and 250° C. (e.g., 70-330° C., 200-330° C., 250-300° C., etc.).

In some embodiments, the cellulose content of the wet cellulose hydrogel can comprise from about 1% to about 10% by weight. In some embodiments, the cellulose content of the wet hydrogel is about 2% to about 9% by weight, about 3% to about 8% by weight, about 4% to about 7% by weight, or about 5% to about 6% by weight. In some embodiments, the cellulose content of the wet hydrogel is about 2% by weight, about 2.5% by weight, about 3.0% by weight, about 3.5% by weight, about 4.0% by weight, about 4.5% by weight, about 5.0% by weight, about 5.5% by weight, about 6.0% by weight, about 6.5% by weight, about 7.0% by weight, about 7.5% by weight, about 8.0% by weight, about 8.5% by weight or about 9.0% by weight.

In some embodiments, the cellulose content of the re-wet cellulose hydrogel is about 40% to about 65% by weight. In some embodiments, the cellulose content of the re-wet hydrogel is about 40% to about 55% by weight, or about 45% to about 55% by weight. In some embodiments, the cellulose content of the re-wet hydrogel is about 40% by weight, about 45% by weight, about 50% by weight, about 55% by weight, about 60% by weight or about 65% by weight.

The water content and thus the cellulose content of the cellulose hydrogel can be determined by thermal gravimetric analysis. For example, samples can be heated from room temperature to about 400° C. and their masses are measured during the heating. The mass lost during the temperature increase reflects the water content and the remainder, the cellulose content.

In some embodiments, the cellulose hydrogel has a thickness of about 10 µm to about 2500 µm. In some embodiments, the thickness is about 50 to about 1000 µm. In some embodiments, the thickness is from about 75 µm to about 500 µm. In some embodiments, the thickness is about 35 µm, about 60 µm, about 85 µm, about 100 µm, about 125 µm, about 175 µm, or about 225 µm. Different thicknesses can be produced, depending on the intended use.

In some embodiments, the cellulose hydrogel can be provided in the desired thickness using a single layer of the hydrogel material, or using multiple layers of the hydrogel material. In some embodiments, the cellulose hydrogel comprises a plurality of layers or plys. For example, a plurality of (i.e. two or more) layers of cellulose hydrogel material, can be bonded together to form a multilaminate structure. In some embodiments, two, three, four, five, six, seven, eight, nine, ten, or more cellulose hydrogel layers are bonded together to provide a multilaminate material. The layers of cellulose hydrogel can be bonded together in any suitable fashion, including dehydrothermal bonding under heated, non-heated or cooled (e.g. lyophilization) conditions, vacuum pressing, using adhesives, glues or other bonding agents, crosslinking with chemical agents or radiation (including UV radiation), or any combination of these with each other or other suitable methods. In some embodiments, the hydrogel of the invention comprises one or more cellulose layers. In one embodiment, the cellulose fibers in a layer are substantially aligned relative to the other cellulose fibers in the same layer. In other embodiments including multiple layers of cellulose fibers, the fibers in each layer are aligned and rotated relative to the fibers in an adjacent layer. In certain embodiments, a cellulose fiber layer is rotated between about 5-90 degrees relative to an adjacent layer. In some embodiments, the cellulose fibers are substantially aligned relative to the other cellulose fibers in the same layer. In some embodiments, the fibers can be aligned by a process selected from the group consisting of wet drawing (stretching wet gels to cause alignment of fibers), syringe pump synthesis (ejecting fibers through an array of syringes forming the gel from these aligned fibers), subjecting the fibers to electric or magnetic fields (fields interact with charged particles on the cellulose), and a combination thereof. In some embodiments, the hydrogel comprises multiple layers of cellulose fibers, wherein the fibers in each layer are rotated relative to the fibers in an adjacent layer.

In some embodiments, the cellulose hydrogel can be a composite comprising cellulose from one or more sources, which can be in the same layer or in different layers. In some embodiments, the cellulose hydrogel is a composite of microcrystalline cellulose from a plant source and bacterial cellulose. In some embodiments, the cellulose hydrogel comprises one or more cellulose fiber layers and one or more layers of a modified cellulose polymer. In some embodiments, the cellulose hydrogel comprises one or more cellulose fiber layers and one or more layers of synthetic polymer. In some embodiments, the cellulose hydrogel comprises one or more layers of cellulose of bacterial origin and one or more layers of cellulose of plant origin.

In some embodiments, the cellulose hydrogel is a composite comprising cellulose and one or more synthetic polymers. In some embodiments, the one or more synthetic polymers are selected from the group consisting of hydroxyethylmethacrylate (HEMA), poly(hydroxyethyl methacrylate) (PHEMA), polyacrylamide, polyethylene glycol (PEG), polyethyleneoxide (PEO), polyacrylonitrile (PAN), polyvinyl alcohol (PVA), poly(vinyl pyrrolidone) (PVP), and silicones.

The synthetic or natural polymer can be added to the cellulose before, during or after the cellulose forms a gel. In some embodiments, the synthetic polymer forms a gel and is added to the cellulose hydrogel in a layered fashion. In some embodiments, the cellulose hydrogel comprises alternating layers of cellulose and one or more synthetic polymers. In some embodiments, the synthetic or natural polymer is layered on top of the cellulose hydrogel.

In some embodiments, the cellulose hydrogel is prepared by a process comprising:

(i) contacting cellulose with a solvent to activate the cellulose;

(ii) optionally removing the solvent from the activated cellulose;

(iii) substantially dissolving the activated cellulose to form a solution; and (iv) allowing the solution to gel.

In some embodiments, the process further comprises: (v) drying the gel and rehydrating the gel, to create a re-wet cellulose hydrogel. In some embodiments, a salt, such as LiCl, is added to step (i) directly, and step (ii) is omitted. In some embodiments, step (ii) is performed, and a solvent is added to the activated cellulose to substantially dissolve it. In some embodiments, the solvent includes a salt, such as LiCl.

In some embodiments, the cellulose content of the solution of (iv) is from about 1.0% to about 6.5% weight/volume (wt/vol). In some embodiments, the cellulose content is from about 1.5% to about 6.0% wt/vol, from about 2.0% to about 5.0% wt/vol, or from about 2.5% to about 3.0% wt/vol. In some embodiments, the cellulose content is about 1.5% wt/vol, about 2.0% wt/vol, about 2.5% wt/vol, about 3.0% wt/vol, about 3.5% wt/vol, about 4.0% wt/vol, about 4.5% wt/vol, about 5.0% wt/vol, about 5.5% wt/vol, about 6.0% wt/vol, or about 6.5% wt/vol.

In some embodiments, the solution gels in a mold or on a flat glass plate and is later removed from the mold and is optionally washed. In some embodiments, the gel is washed for several hours in running water to remove all salts/solvents. In one embodiment, the mold is a contact lens mold.

In some embodiments, the solvent of step (i) is selected from the group consisting of dimethylacetamide, water, methanol, acetone, ethanol and a combination of water and ethanol. Any suitable technique can be used for removing the solvent of step (i), if desired, including decanting the solvent from the reaction mixture.

The activated cellulose can be substantially dissolved in any solvent suitable for such dissolution. In some embodiments, the solvent for dissolving the cellulose is selected from the group consisting of cupriethylenediamine (CED), cadmiumethylenediamine (Cadoxen), LiCl/dimethylacetamide (LiCl/DMAc), $Ca(SCN)_2$/water, 1-butyl-3-methylimidazolium chloride (BmimCl), NaOH/water, N-methyl-morpholine-N-oxide (NMMO)/water, and 1-allyl-3-methyllimidazolium chloride. As indicated above, in some embodiments, a salt, such as LiCl, is added to step (i) directly. The addition of the salt to step (i) can result in the activated cellulose becoming substantially dissolved in the solvent.

In some embodiments, the solution of activated cellulose is allowed to gel overnight, but other suitable gelling times also may be used. In some embodiments, the wet hydrogel is gelled in a mold or on a flat plate. In some embodiments, the wet hydrogel solution or mixture obtained from the step of substantially dissolving the activated cellulose in a solvent can be transferred directly to the mold or flat plate, for example, for gelling without additional treatment steps, or at least chemical treatment steps.

Any suitable technique for drying, if desired, the gel can be used. In some embodiments, the gel is dried by: 1) freeze drying (lyophilization); 2) drying in a hot press between two heated platens while applying an amount of pressure; 3) a solvent exchange process 4) supercritical $CO_2$; 5) air drying; and 6) a combination of the above techniques.

In one embodiment, the gel can be dried in a hot press between two heated platens, preferably lined with Teflon film, while applying a small amount of pressure. In some embodiments, the drying temperature can be in the range of about 25-90° C., and the drying time varies based on the hydrogel's thickness. In some embodiments, sheets of cellulose hydrogel are dried or dehydrated between glass plates lined with Teflon film in an oven above 100° C. for several hours, preferably about 5 hours.

In some embodiments, the gel is dried by a solvent exchange followed by supercritical $CO_2$. When drying the gel by a solvent exchange process followed by supercritical $CO_2$, in one embodiment, gels are immersed in a solvent, for example, methanol, and placed under a vacuum in a chamber. The gel then undergoes a purge cycle and the methanol is replaced by liquid $CO_2$. Solvents other than methanol can also be used, including acetone.

Any suitable technique or conditions for rehydrating the gel may be used, including, in some embodiments, rehydrating the gel in tap or deionized water for several hours. In some embodiments, the gel is rehydrated in a substantially sterile aqueous solution, such as saline, or buffered saline. In some embodiments, the gel is rehydrated in biological growth medium such as DMEM.

In accordance with certain embodiments of the present invention, a process for preparing a wet cellulose hydrogel can comprise: (i) activating the cellulose, wherein the activating step comprises contacting the cellulose with a solvent (e.g., as discussed above) to activate the cellulose for a time duration from about 2 hours to about 30 hours; (ii) substantially dissolving the activated cellulose to form a solution; and (iii) gelling the solution to form a gel, wherein the gelling step comprises allowing the solution to gel in an environment comprising a relative humidity from about 30% to about 80% at 35° C. In certain embodiments, the process is devoid of any dehydrating or drying step.

In accordance with certain embodiments, the activating step comprises contacting (e.g., soaking, stirring, mixing, etc.) the cellulose with a solvent (e.g., N,N-dimethylacetamide) to activate the cellulose for about 10 hours to about 20 hours. For instance, the cellulose can be added to a solvent (e.g., N,N-dimethylacetamide) and stirred or thoroughly mixed in the solvent to activate the cellulose. In certain embodiments, the activation step comprises a single-step activation. That is, the single-step activation step is devoid of a plurality of solvent exchange steps, in which the cellulose is subjected to more than a single activation step. In accordance with certain single-step activation steps, the final cellulose hydrogel surprisingly provides increased tensile strengths compared to hydrogels produced using a multi-step activation process.

The single-step activation step, according to certain embodiments, can comprise a contacting time of about 2 hours to about 196 hours. For instance, the single-step activation step according to certain embodiments can comprise a contacting time comprising from at least any of the following: 2, 4, 6, 8, 10, 12, 16, 20, 24, 30, and 32 hours and/or at most about any of the following 196, 150, 120, 100, 90, 75, and 50 hours (e.g., 2-30 hours, 8-24 hours, 16-50 hours, etc.).

In accordance with certain embodiments, the step of substantially dissolving the activated cellulose to form a solution comprises adding and mixing a salt, such as LiCl to the activated cellulose. The dissolution step can comprise a mixing time from at least any of the following: 2, 4, 5, 6, 8, 10, and 15 minutes and/or at most about any of the following 60, 45, 30, and 20 minutes (e.g., 2-60 minutes, 5-15 minutes, etc.).

The activated cellulose can be substantially dissolved in any solvent suitable for such dissolution. In some embodiments, the solvent for dissolving the cellulose is selected from the group consisting of cupriethylenediamine (CED), cadmiumethylenediamine (Cadoxen), LiCl/dimethylacetamide (LiCl/DMAc), $Ca(SCN)_2$/water, 1-butyl-3-methylimidazolium chloride (BmimCl), NaOH/water, N-methyl-morpholine-N-oxide (NMMO)/water, and 1-allyl-3-methylimidazolium chloride. As indicated above, in some embodiments, a salt, such as LiCl, is added to step (i) directly. The addition of the salt to step (i) can result in the activated cellulose becoming substantially dissolved in the solvent The gelling step, according to certain embodiments of the present invention, can comprise allowing the solution to gel in an environment comprising a relative humidity from about 10% to about 95% at 35° C. For instance, the gelling step can comprise allowing the solution to gel in an environment comprising a relative humidity from at least any of the following: 10, 20, 30, 40, 50, 60, and 70% at 35° C. and/or at most about any of the following 95, 90, 85, 80, 75, and 70% at 35° C. (e.g., 50-95% at 35° C., 70-80% at 35° C., etc.). In accordance with certain embodiments, an environment comprising a higher gelation humidity (e.g., above 40, 50, 60, 70, or 80% at 35° C.) can provide the final hydrogel with an increased ultimate tensile strength (UTS) and strain to break, which can be particularly desirable for occular applications (e.g., corneal bandage) according to certain embodiments of the present invention.

Certain embodiments according to the present invention can comprise gelling (or allowing to gel) the cellulose solution in a mold, in which the gelled material (e.g., wet hydrogel) is later removed and optionally washed. In certain embodiments, the mold is a contact lens mold The cellulose hydrogels of the invention can be provided and packaged in a dehydrated or hydrated state. Dehydration of the cellulose hydrogel can be achieved by any means known in the art. For example, dehydration can be accomplished by lyophilization, including, for instance, freeze-drying or evaporative cooling techniques, air-drying, heating, or the like. When desired, a suitable aqueous medium can be used to rehydrate a dehydrated material of the invention prior to use. In some embodiments, the aqueous medium can be pure water or a physiologically acceptable solution such as phosphate-buffered saline (PBS).

In some embodiments, the packaging material is impermeable to water to prevent the cellulose hydrogel membrane from drying out, and be able to withstand a sterilization process, if desired.

In some embodiments, the cellulose hydrogel membrane is sterilized before or after packaging. Such sterilization procedures can include, for example, gamma irradiation and electron beam sterilization or autoclave.

The cellulose hydrogels of the invention have many uses, including, for example, as contact lenses, wound dressings, including transparent bandages, ocular bandages, corneal onlays, corneal inlays, and for corneal replacement, including partial or full-thickness corneal implants. Other uses of the cellulose hydrogels include, without limitation, wound healing applications, tissue regenerative applications, cardiovascular applications, orthopedic applications, and urologic applications. Still other applications of the cellulose hydrogels of the invention include drug delivery systems, including sustained-release delivery systems, osmotic membranes (for drug delivery or other uses), chemical or biological sensor membranes, transparent structural material, diapers or sanitary napkins due to their absorbent properties, breast or other cosmetic implants, as well as other medical devices in which the cellulose hydrogels of the invention would be suitable.

In some embodiments, the cellulose hydrogel is used as a soft contact lens for vision correction. In some embodiments, the cellulose hydrogel membrane has a refractive index of between about 1.3 and about 1.5. In some embodiments, the refractive index is about 1.30, 1.31, 1.32, 1.33, 1.34, 1.35, 1.36, 1.37, 1.38, 1.39, or 1.40.

The cellulose hydrogel for use as a contact lens can be produced using various molds, as is known in the art. Examples of such molds and their methods of production may be found in U.S. Pat. Nos. 4,565,348, 4,640,489, 4,495,313, and 7,833,443, which are incorporated herein by reference in their entirety.

In some embodiments, methods for making a contact lens comprising the cellulose hydrogel of the invention involve placing a sheet of the hydrogel over a cavity of a first half of a lens mold in the presence of a suitable buffer, for example, PBS. Force can then applied, by a spring clamp, for example, to keep the first half together with the second half of the mold. The mold can then be placed in a humidity chamber having a suitable relative humidity and temperature. In some embodiments, the relative humidity is from about 35% to about 55% (for example 40%), while the temperature is from about 30° C. to about 50° C. (for example, about 40° C.). After a sufficient period of time, about 48 hours in one embodiment, the clamp or other force applied can be removed and the mold opened. Any excess cellulose and gel can then be trimmed, as desired. The lens can then be stored in a suitable buffer, including, for example, PBS. In particular, one method for making a cellulose hydrogel contact lens in accordance with the invention is described in Example 5 and illustrated in FIG. 24.

In some embodiments, after the contact lens is removed from the mold it may undergo additional processing steps such as trimming, edge chamfering, cleaning, sterilization, hydration, polishing, coating with an antireflective coating, and packaging for shipment. In some embodiments, the contact lens will be coated or imbibed with an adjuvant, for example a neutral alkane mineral oil, such as DRAKEOL-20 or SOOTHE, which augments and fortifies the oil layer of the tear film by reducing evaporation of the aqueous component of the tear film while lubricating the action of the eye lids.

In some embodiments, the contact lens cellulose hydrogel has a refractive index of about 1.34, a base curve radius of from about 7.9 to about 8.4 mm, a center thickness of between about 65 and 110 microns, and a spherical front radius of from about 8.6 to 9.0 mm.

In some embodiments, the present invention also provides kits and packaging and solutions comprising the cellulose hydrogel contact lens of the invention, and optionally instructions for their use, as described further below.

In some embodiments, the cellulose hydrogel contact lenses are packaged in blister packages or glass vials. In some embodiments, the cellulose hydrogel membranes are stored in saline or deionized water in the packages. In some embodiments, the cellulose hydrogel contact lenses may tend to stick to itself and to the package. Therefore, in some embodiments, the packaging solutions for blister-packs are formulated to reduce or eliminate folding and sticking. In some embodiments, the packaging solutions may include a polymer to improve comfort of the cellulose hydrogel membrane. In some embodiments, polyvinyl alcohol (PVA) is added to packaging solution. The packaging solution can include polyethylene oxide (PEO)/polypropylene oxide (PPO) block copolymers, such as poloxamers or poloxamines, as disclosed in U.S. Pat. No. 7,832,856.

In some embodiments, the contact lenses are packaged in a blister pack. Examples of typical art blister packs are shown in U.S. Pat. Nos. 5,704,468, 4,392,569, 5,620,088, 5,620,088, 4,691,820, 5,823,327, 5,853,085, and EP Publication Nos. 1092645 A1, 1092645, and 0129388, which are incorporated by reference herein in their entirety. In some embodiments, the lenses are packaged in a blister pack polypropylene receptacle (herein after referred to as a "boat"), topped by a multilayer film consisting of polyethylene, aluminum, a bonding agent and polypropylene. In some embodiments, the boat is an injection molded plastic which has high stiffness but is capable of limited elastic deflection and includes a preformed recess. The boat is filled with a suitable storage solution, such as saline, and receives a single lens in situ. In some embodiments, blister pack is autoclaved using steam and pressure to terminal sterility. These blister packs can be presented to the subject or health care provider in boxes of individual packs or as multiple blister strips. In some embodiments, the lenses are kept hydrated while in the package. Preferably, the package is well sealed and should minimize water vapor transmission through the boat and laminated layer to maximize the shelf life and prevent drying out of the contact lenses contained therein. In use, the user removes the laminated material from a flange formed on the boat by peeling back the cover to expose the cellulose hydrogel membranes immersed in a hydrating solution.

In at least some embodiments, the contact lenses will be corrective of vision and can be single vision, bifocal, trifocal, and progressive. In some embodiments, the peripheral edges to the lenses will be chamfered or beveled to round the peripheral edges so as to prevent snagging onto the eyelid wiper during blinking.

Additionally, in other embodiments of the present invention, the cellulose hydrogel can be configured or used for other treatments of the eye of a subject. In some embodiments, the hydrogel can be used to repair or replace the cornea and/or conjunctiva tissue of the eye. For example, the biocompatible material may be implanted in the treatment of corneal epithelial defects such as corneal ulcers (breaks in the outer layer of the epithelium of the cornea) and/or for ocular surface reconstruction.

The cellulose hydrogels of the invention also can be useful for replacing all or a portion of the cornea of an eye. In some embodiments, at least a portion of a damaged or diseased cornea of a subject is removed, and the cellulose hydrogel of the invention is implanted in its place. The implant can be attached to the eye in any suitable fashion. In some embodiments, the implant is attached using sutures. In some embodiments, the subject is a human or other mammal. Corneal implants incorporating a cellulose hydrogel of the present invention may be provided in a shape corresponding to all or a portion of a native cornea. The implant can be provided as single-layer or multiple-layer of cellulose hydrogel material to provide the desired thickness.

In some embodiments, the hydrogel can be used as a corneal onlay. As used herein, a "corneal onlay" is an ophthalmic implant or device configured for placement between the epithelium or an epithelial cell layer and Bowman's membrane of an eye. In comparison, a contact lens is configured for placement over the epithelium of an eye. A corneal onlay may thus be located after placement entirely over the Bowman's membrane, or may include one or more portions extending into the Bowman's membrane. Such portions preferably constitute a minor portion of the device, for example, less than 50% of the area or volume of the device.

In some embodiments, the hydrogel can be used as a corneal inlay. As used herein, a "corneal inlay" is a device or implant configured to be placed in the stroma of an eye. Corneal inlays may be placed in the stroma by forming a flap or a pocket in the stroma. Corneal inlays are placed below the Bowman's membrane of an eye.

Medical implants incorporating the cellulose hydrogel of the invention can be provided in a variety of shapes, including planar (e.g. sheet-form) and non-planar shapes. Exemplary non-planar shape implants include implants configured to have a concave surface, e.g., to substantially correspond to a convex surface of eye tissue against which the implant will reside. Thus, certain implants of the invention will have a convexo-concave structure in their relaxed state, for example in the case of a parabolic shape or a segment of a sphere (e.g. hemisphere). Such an implant may in some cases serve as a lens.

In some embodiments, the cellulose hydrogel membrane comprises one or more bioactive agents. In some embodiments, the one or more bioactive agents aid in wound healing, reduce or alleviate pain, prevent or attack infection, and/or assist in tissue repair or regeneration. In some embodiments, the cellulose hydrogel membrane provides a controlled delivery of the bioactive agent to the underlying wound or tissue to aid in the treatment, management, and eventual healing of the wound and/or to alleviate pain. In some embodiments, the bioactive agent is released immediately from the cellulose hydrogel membrane upon contact with the wound. In some embodiments, the bioactive agent is released over a sustained period of time, for example, using polymer microcapsules that contain a drug and are embedded in the gel.

The term "bioactive agent," as used herein, refers to a molecule or compound which exerts a physiological, therapeutic or diagnostic effect in vivo. Bioactive agents may be organic or inorganic. Representative examples include proteins, peptides, carbohydrates, lipids, nucleic acids and fragments thereof, anti-viral compounds, anti-inflammatory compounds, antibiotic compounds such as antifungal and antibacterial compounds, cell differentiating agents, analgesics, contrast agents for medical diagnostic imaging, enzymes, cytokines, anaesthetics, antihistamines, agents that act on the immune system, hemostatic agents, hormones, angiogenic or anti-angiogenic agents, neurotransmitters, therapeutic oligonucleotides, viral particles, vectors, growth factors, retinoids, cell adhesion factors, extracellular matrix glycoproteins (such as laminin), osteogenic factors, antibodies and antigens, steroids, painkillers. The bioactive agents can be in their free base or acid form, or in the form of salts, esters, or any other pharmacologically acceptable derivatives, enantomerically pure forms, tautomers or as components of molecular complexes. The amount of bioactive agents to be incorporated in the composition can vary depending on the particular bioactive agent, the desired effect, and the time span for which the composition is to be administered.

In some embodiments, the cellulose hydrogel membrane comprises one or more antibiotics. The antibiotics can be present in amounts that are effective to either prevent or treat infection in the wound area, surrounding tissues, or systemically. Non-limiting examples of particular classes of antibiotics that can be included in the cellulose hydrogel membrane include aminoglycosides (e.g., tobramycin, amikacin, gentamicin, kanamycin, netilmicin, tobramycin, streptomycin, azithromycin, clarithromycin, erythromycin, neomycin, erythromycin estolate/ethylsuccinate, gluceptate/lactobionate/stearate), beta-lactams such as penicillins (e.g., penicillin G, penicillin V, methicillin, nafcillin, oxacillin, cloxacillin, dicloxacillin, ampicillin, amoxicillin, ticarcillin, carbenicillin, mezlocillin, azlocillin and piperacillin), cephalosporins (e.g., cephalothin, cefazolin, cefaclor, cefamandole, cefoxitin, cefuroxime, cefonicid, cefmetazole, cefotetan, cefprozil, loracarbef, cefetamet, cefoperazone, cefotaxime, ceftizoxime, ceftriaxone, ceftazidime, cefepime, cefixime, cefpodoxime, and cefsulodin), fluoroquinolones (e.g., ciprofloxacin), carbepenems (e.g., imipenem), tetracyclines (e.g., doxycycline, minocycline, tetracycline), macrolides (e.g., erythromycin and clarithromycin), monobactams (e.g., aztreonam), quinolones (e.g., fleroxacin, nalidixic acid, norfloxacin, ciprofloxacin, ofloxacin, enoxacin, lomefloxacin and cinoxacin), glycopeptides (e.g., vancomycin, teicoplanin), chloramphenicol, clindamycin, trimethoprim, sulfamethoxazole, nitrofurantoin, rifampin and mupirocin, and polymyxins, such as PMB, oxazolidinones, imidazoles (e.g., miconazole, ketoconazole, clotrimazole, econazole, omoconazole, bifonazole, butoconazole, fenticonazole, isoconazole, oxiconazole, sertaconazole, sulconazole and tioconazole), triazoles (e.g., fluconazole, itraconazole, isavuconazole, ravuconazole, posaconazole, voriconazole, terconazole and albaconazole), thiazoles (e.g., abafungin), and allylamines (e.g., terbinafine, naftifine and butenafine), echinocandins (e.g., anidulafungin, caspofungin and micafungin). Other antibiotics can include polygodial, benzoic acid, ciclopirox, tolnaftate, undecylenic acid, flucytosine or 5-fluorocytosine, griseofulvin, and haloprogin.

In some embodiments, the cellulose hydrogel membrane comprises one or more anesthetics. In some embodiments, the one or more anesthetics can include procaine, benzocaine, chloroprocaine, cocaine, cyclomethycaine, dimethocaine, piperocaine, propoxycaine, procaine, novocaine, proparacaine, tetracaine, lidocaine, articaine, bupivacaine, cinchocaine, etidocaine, levobupivacaine, mepivacaine, prilocalne, ropivacaine, and trimecaine. In some embodiments, the anesthetic is a combination of lidocaine and prilocalne.

In some embodiments, the cellulose hydrogel membrane comprises one or more analgesics. The analgesics can include opiates and analogues thereof. Exemplary opiates include morphine, codeine, oxycodone, hydrocodone, dihydromorphine, pethidine, buprenorphine, tramadol, fentanyl and venlafaxine.

In some embodiments, the cellulose hydrogel membrane comprises one or more hemostatic agents. In one embodiment, the hemostatic agent is thrombin.

In some embodiments, the cellulose hydrogel membrane comprises one or more anti-inflammatory compounds. Anti-inflammatory compounds can include agents such as hydrocortisone, cortisone, dexamethasone, fluocinolone, triamcinolone, medrysone, prednisolone, flurandrenolide, prednisone, halcinonide, methylprednisolone, prednisone, halcinonide, methylprednisolone, fludrocortisone, corticosterone, paramethasone, betamethasone, ibuprophen, naproxen, fenoprofen, fenbufen, flurbiprofen, indoprofen, ketoprofen, suprofen, indomethacin, piroxicam, aspirin, salicylic acid, diflunisal, methyl salicylate, phenylbutazone, sulindac, mefenamic acid, meclofenamate sodium and tolmetin.

In some embodiments, the cellulose hydrogel membrane comprises one or more antihistamines. The one or more antihistamines can include, for example, diphenhydramine, dimenhydrinate, perphenazine, triprolidine, pyrilamine, chlorcyclizine, promethazine, carbinoxamine, tripelennamine, brompheniramine, hydroxyzine, cyclizine, meclizine, clorprenaline, terfenadine and chlorpheniramine.

In some embodiments, the cellulose hydrogel membrane comprises one or more growth factors in amounts that are effective to promote wound healing and/or tissue repair or regeneration. Non-limiting examples of growth factors include vascular endothelial growth factor ("VEGF"), nerve growth factor, such as NGF-beta, platelet-derived growth factor (PDGF), fibroblast growth factors, including, for instance, aFGF and bFGF, epidermal growth factor (EGF), keratinocyte growth factor, tumor necrosis factor, transforming growth factors (TGF), including, among others, TGF-alpha and TGF-beta, including TGF-beta1, TGF-beta2, TGF-beta3, TGF-beta4, or TGF-beta5, insulin-like growth factors-I and -II (IGF-I and IGF-II), des(1-3)-IGF-I (brain IGF-I), neurotrophin-3 (NT-3) and brain-derived neurotrophic factor (BDNF).

In some embodiments, the cellulose hydrogel membrane comprises a bioactive agent selected from the group consisting of hyaluronan, β-1,3 glucan, carboxymethylcellulose, chitosan, a growth factor, a hormone and mixtures and combinations thereof. In some embodiments, the bioactive agent is a steroid, anti-inflammatory, an antibiotic, a narcotic, a non-steroidal anti-inflammatory agent, an acetaminophen and combinations or mixtures thereof.

In some embodiments, the cellulose hydrogel membrane comprises one or more bioactive agents selected from the group consisting of one or more antibiotics, one or more analgesics, one or more anesthetics, one or more growth factors, and combinations thereof.

In some embodiments, the cellulose hydrogel membrane can further include nutritional agents, such as vitamins, essential and non-essential amino acids, essential and non-essential fats and combinations thereof.

The one or more bioactive agents can be added before, during, or after formation of the cellulose hydrogel membrane, and can also be added directly to the cellulose hydrogel membrane while it is present on the wound. In some embodiments, the cellulose hydrogel membrane is removed from the wound, and the one or more bioactive agents are added thereto, and the cellulose hydrogel membrane is then placed back on the wound. In some embodiments, the incorporation of the bioactive agent occurs after formation of the cellulose hydrogel membrane. In some embodiments, the one or more bioactive agents is added to the cellulose hydrogel membrane and becomes incorporated therein. In some embodiments, the bioactive agent is coated on the surface of the cellulose hydrogel membrane. In some embodiments, the cellulose hydrogel membrane is contacted with or immersed in a solution comprising the bioactive agent, resulting in incorporation of the bioactive agent throughout the entire cellulose hydrogel membrane or some part thereof.

In some embodiments, the bioactive agent is encapsulated within the cellulose hydrogel membrane by one or more encapsulating agents to facilitate delivery and/or stabilization of the bioactive agent. By "encapsulated," it is meant association with an encapsulating agent. The association may be effected by a variety of means, including covalent bonding to the encapsulating agent, preferably with a cleavable linkage, non-covalent bonding, and trapping the agent in the interior of the encapsulating agent. The one or more bioactive agents can be encapsulated using known encapsulating agents and methods. In some embodiments, the one or more bioactive agents are encapsulated in one or more lipid carriers, liposomes, lipid micelles, lipoprotein micelles, lipid-stabilized emulsions, cyclodextrins, polymer nanoparticles, polymer microparticles, block copolymer micelles, polymer-lipid hybrid systems, derivatized single chain polymers or combinations thereof. In some embodiments, different bioactive agents are associated with the same encapsulating agent and can also be encapsulated together. In other embodiments, different bioactive agents are encapsulated with different agents, for example, in cases where a different release profile is desired.

In some embodiments, the cellulose hydrogel membrane comprises one or more buffer substances to maintain the membrane within specified pH ranges. In some embodiments, the cellulose hydrogel membrane is maintained between a pH range of about 4 to about 9, between a range of about 6-8, or around a pH of about 7.

In some embodiments, the cellulose hydrogel membrane can have a backing material attached thereto. In some embodiments, the backing material provides additional protection and/or support for the cellulose hydrogel membrane. In some embodiments, the backing can serve to prevent visual observation of the wound through the transparent cellulose hydrogel membrane, especially in situations where it is not desirable for the wound to be visible (or for the eye to be exposed to light). In some embodiments, the backing is not permanent, and can be freely removable and can be reattached, if needed. For example, in some embodiments, the backing can be removed by a health care provider to assess the progress of wound healing by inspecting the wound through the cellulose hydrogel membrane. In some embodiments, the backing is in the form of a layer or more of cellulose (e.g., microbial or plant-based), a polyester, a polyurethane, a polyethylene glycol or derivative thereof, a vinyl pyrrolidone acrylic, a methacrylic acid, a silicone isobutylene, a isoprene or a styrene or combinations thereof. In some embodiments, the cellulose can be modified to make it compatible or adherent to the backing material.

In some embodiments, the cellulose hydrogel membrane stably adheres to the wound site and/or nearby tissue(s). In some embodiments, the cellulose hydrogel membrane is coupled to a biocompatible adhesive composition that is capable of adhering to a biological material. In some embodiments, one or more functional groups can be added to the cellulose, enabling improved adhesion directly to the wound site or surrounding tissue or enabling covalent or non-covalent attachment to an adhesive that adheres directly to the wound site or surrounding tissue. In one embodiment, the cellulose is functionalized with anime groups.

For example, in one embodiment, the cellulose can be functionalized with amine groups by (i) contacting cellulose with a solution of epibromohydrin and mixing; (ii) removing the solution of epibromohydrin and rinsing the cellulose with a first solvent; (iii) transferring the cellulose to neat 4,7,10 trioxa-1,13-tridecamine and mixing it for a period of time and (iv) washing the cellulose with a second solvent. In some embodiments, the mixing of step (iii) is performed at a temperature from about 35° C. to about 50° C. In some embodiments, the mixing is performed at a temperature from about 35° C. to about 50° C. for at least one hour, at least 2 hours, at least 3 hours, at least 4 hours, at least 5 hours, at least 6 hours, at least 7 hours, or at least 8 hours. In some embodiments, the mixing is performed at a temperature from about 18° C. to about 35° C. In some embodiments, the mixing is performed at a temperature from about 18° C. to about 35° C. for at least one hour, at least 4 hours, at least 6 hours, at least 8 hours, at least 12 hours, at least 14 hours, at least 16 hours, or at least 18 hours or at least 24 hours. In some embodiments, the first solvent of (ii) and second solvent of (iv) are the same. In some embodiments, the first and second solvent is methanol. In some embodiments, the epibromohydrin is in 1,4 dioxane. In some embodiments, the concentration of epibromohydrin ranges from about 5% to about 50%, from about 10% to about 40%, or from about 15% to about 35%. In some embodiments, the concentration of epibromohydrin is about 20%.

The cellulose hydrogel membranes, according to certain embodiments of the present invention, can have one or more desirable physical properties for use in wound healing compositions, including tensile strength, tear strength, suture retention strength, transparency, puncture resistance, oxygen permeability, low cellulose content and high water content, and combinations thereof. In some embodiments of the invention, the cellulose hydrogel membranes are "wet" and in some embodiments, the cellulose hydrogel membranes are "rewet."

In some embodiments, the cellulose hydrogel membrane can comprise one or more synthetic or natural polymers. In some embodiments, the synthetic polymers are selected from the group consisting of hydroxyethylmethacrylate (HEMA), poly(hydroxyethyl methacrylate) (PHEMA), polyacrylamide, polyethylene glycol (PEG), polyethyleneoxide (PEO), polyacrylonitrile (PAN), polyvinyl alcohol (PVA), poly(vinyl pyrrolidone) (PVP), and silicones.

The synthetic or natural polymer can be added to the cellulose before, during or after the cellulose forms a gel. In some embodiments, the synthetic or natural polymer forms a gel and is added to the cellulose hydrogel in a layered fashion. In some embodiments, the cellulose hydrogel comprises alternating layers of cellulose and one or more synthetic or natural polymers. In some embodiments, the synthetic or natural polymer is layered on top of the cellulose hydrogel membrane.

In some embodiments, the natural polymer is collagen. In some embodiments, the cellulose and collagen composite can be prepared by a process that includes an immersion step, an annealing step, and a rehydration step. In some embodiments, a cellulose sheet is dried (for example, with a paper towel) to remove any excess water. Next, in some embodiments, the cellulose sheet can be immersed in either: (1) culture Medium+an acid collagen solution (e.g., 0.5%) (2) acid collagen solution (e.g., 0.5%), or (3) acid collagen solution (e.g., 0.5%)+methylglyoxal solution (e.g., 0.5%) (methylglyoxal promotes the collagen cross-linking) for a period of time, such as 30 minutes. In some embodiments, the specimens are then incubated (e.g., at 37° C., 5% $CO_2$ for two hours). Then, in some embodiments, the samples are dried under controlled conditions (e.g., at 40° C., 60% RH (relative humidity) for about 0.5 weeks). Finally, in some embodiments, the samples are rehydrated with aqueous solution (e.g., phosphate buffered saline).

In some embodiments, the cellulose hydrogel can be provided in the desired thickness using a single layer of the hydrogel material, or using multiple layers of the hydrogel material. In some embodiments, the cellulose hydrogel membrane comprises a plurality of layers or plys. For example, a plurality of (i.e. two or more) layers of cellulose hydrogel material, can be bonded together to form a multilaminate structure. In some embodiments, two, three, four, five, six, seven, eight, nine, ten, or more cellulose hydrogel layers are bonded together to provide a multilaminate material. The layers of cellulose hydrogel can be bonded together in any suitable fashion, including dehydrothermal bonding under heated, non-heated or cooled (e.g. lyophilization) conditions, vacuum pressing, using adhesives, glues or other bonding agents, crosslinking with chemical agents or radiation (including UV radiation), or any combination of these with each other or other suitable methods.

In some embodiments, the cellulose hydrogel membrane can be a composite comprising cellulose from one or more sources, which can be in the same layer or in different layers. In some embodiments, the cellulose hydrogel membrane is a composite of microcrystalline cellulose from a plant source and bacterial cellulose. In some embodiments, the cellulose hydrogel comprises one or more cellulose fiber layers and one or more layers of a modified cellulose polymer. In some embodiments, the cellulose hydrogel comprises one or more cellulose fiber layers and one or more layers of synthetic polymer. In some embodiments, the cellulose hydrogel comprises one or more cellulose fiber layers and one or more layers of collagen. In some embodiments, the cellulose hydrogel membrane comprises one or more layers of cellulose of bacterial origin and one or more layers of cellulose of plant origin. In some embodiments, the bacterial cellulose layers are oriented to be on the side of the cellulose hydrogel membrane that makes direct contact with the wound site, while the one or more layers comprising cellulose of plant origin are oriented on top of the bacterial cellulose layer(s), i.e., directed further away from the wound site.

In some embodiments, the biocompatible cellulose hydrogel membrane is in the shape of a contact lens for certain ocular applications in wound healing.

The cellulose hydrogels of the invention can be provided and packaged in a dehydrated or hydrated state. Dehydration of the cellulose hydrogel can be achieved by any means known in the art. For example, dehydration can be accomplished by lyophilization, including, for instance, freeze-drying or evaporative cooling techniques, air-drying, heating, or the like. When desired, a suitable aqueous medium can be used to rehydrate a dehydrated material of the invention prior to use. In some embodiments, the aqueous medium can be pure water or a physiologically acceptable solution such as phosphate-buffered saline (PBS).

In some embodiments, the packaging material is impermeable to water to prevent the cellulose hydrogel membrane from drying out, and be able to withstand a sterilization process, if desired.

In some embodiments, the cellulose hydrogel membrane is sterilized before or after packaging. Such sterilization procedures can include, for example, gamma irradiation and electron beam sterilization or autoclave.

The invention further provides methods of treating a wound in a subject in need thereof, comprising contacting the wound with an effective amount of a biocompatible cellulose hydrogel membrane of the invention.

All types of wounds can be treated with the biocompatible cellulose hydrogel membrane of the invention. Examples of wound types for which the biocompatible cellulose hydrogel membrane may be used include, but are not limited to skin wounds, ocular wounds, burn wounds, chronic wounds, and ulcers. Additional examples of wounds include wounds caused by laser surgery, chemical burns, cancer treatments, biopsy excision sites, scars from pathogens, gunshot or knife stabbings, cosmetic surgery and reconstructive surgery.

In one embodiment the wound is a cutaneous wound. Examples of cutaneous wounds include burn wounds, neuropathic ulcers, pressure sores, venous stasis ulcers, and diabetic ulcers.

In some embodiments, the wound to be treated is a skin wound. In some embodiments, the skin wound is treated by implanting to the wound a composition comprising a biocompatible cellulose hydrogel membrane.

In some embodiments, the composition for skin wound healing can include one or more bioactive agents selected from the group consisting of hyaluronan, β-1,3 glucan, carboxymethylcellulose, chitosan, peptides, growth factors, hormones and combinations thereof. In some embodiments, the methods of the invention provide for treating a first, second or third degree wound, by attaching to a wound a wound healing composition comprising a biocompatible cellulose hydrogel membrane comprising at least one bioactive agent, wherein the active agent is disposed within, on or about the biocompatible cellulose hydrogel membrane before, during or after the manufacture thereof.

In some embodiments, the biocompatible cellulose hydrogel can be applied to donor sites (e.g., sites that a physician uses for harvesting skin for grafting in burns) or partial thickness wounds (e.g., second degree burns, surgical wounds or wounds which still have the most of the dermis intact which can regenerate from the wound site).

The biocompatible cellulose hydrogel membrane of the present invention can also be used in the treatment of burns, particularly intervention at the earliest possible time after the actual injury. In some embodiments, the wound to be treated is a skin burn wound. In some embodiments, the wound to be treated is a first degree, second degree or third degree burn, or some combination thereof.

In some embodiments, the biocompatible cellulose hydrogel is provided in sterile form by the appropriate personnel having the biocompatible cellulose hydrogel on hand as an immediate temporary cover for all types of injuries, including burn injuries, physical wounding such as gunshots, knife cuts, bruises, contusions, lacerations, etc.

In some embodiments, the biocompatible cellulose hydrogel has the potential to stop the bleeding of wounds (haemostasis), and can include agents that promote clotting, such as thrombin. In some embodiments, the biocompatible cellulose hydrogel can also prevent the entry of bacteria into the wound and serve as a physical barrier.

In some embodiments, the invention provides methods of treating a wound wherein the cellulose hydrogel membrane is permanently implanted into a wound site, wherein the implanted cellulose hydrogel membrane becomes at least partially integrated into the wound site. In some embodiments, the cellulose hydrogel membrane becomes permanently integrated into the wound site. Some wounds which might require permanent integration of the biocompatible cellulose hydrogel membrane include severe cornea injuries, where full or partial corneal replacement is desired.

In another embodiment, the invention provides a method which includes the treatment of wounds by implanting a biocompatible cellulose hydrogel membrane of the invention into a wound site, wherein at least part of the cellulose hydrogel membrane becomes permanently implanted and the cellulose hydrogel membrane is configured to fit the shape of the wound site where it is implanted. For example, the surface of the wound site can be scanned to determine such parameters as width, length, depth and other surface characteristics at the site (e.g., crevices, bones, arteries/veins, curvature, texture). In some embodiments, a mold is created based on these dimensions and used in the manufacture of the cellulose hydrogel membrane. In some embodiments, one or more additional biocompatible cellulose hydrogel membranes can be produced to serve as replacements for the prior biocompatible cellulose hydrogels during the healing of the wound, e.g., in cases where the wound may take days, weeks or even months to heal and/or for patients that have slow wound healing processes. In some embodiments, the biocompatible cellulose hydrogel comprises reservoirs for the external addition of one or more agents, including cells, solutions, and/or bioactive agents.

In some embodiments, the cellulose hydrogel membrane is biocompatible and enables growth of cells on or within the cellulose hydrogel membrane to facilitate wound healing.

In some embodiments, the cells are seeded onto the cellulose hydrogel membrane before, during or after implantation of the cellulose hydrogel membrane. The cells can be of any cell type, and can include stem cells, undifferentiated cells, precursor cells, as well as fully differentiated cells and combinations thereof. In some embodiments, the cells comprise cell types selected from the group consisting of keratocytes, keratinocytes, fibroblast cells, epithelial cells and combinations thereof. In some embodiments, the cells are selected from the group consisting of stem cells, progenitor cells, precursor cells, connective tissue cells, epithelial cells, muscle cells, neuronal cells, endothelial cells, fibroblasts, keratinocytes, smooth muscle cells, stromal cells, mesenchymal cells, immune system cells, hematopoietic cells, dendritic cells, hair follicle cells and combinations thereof. In some embodiments, the cells from the wound site use the cellulose hydrogel membrane as a scaffold to grow and migrate in the wound bed. Bioactive agents can be added to the cellulose hydrogel membrane to affect various activities or properties of the cells, such as cell growth and proliferation, cell adhesion, differentiation, migration, maintenance of undifferentiated states, secretion of extracellular matrix, and secretion of molecules, including growth factors, prostaglandins, cytokines and the like.

In some embodiments, the wound is an ocular wound. Ocular wounds to be treated can include non-penetrating injuries to the cornea (such as abrasions, foreign bodies from explosions, etc), penetrating injuries, for example from blasts or projectiles, or chemical exposure. In some embodiments, the ocular injury is a corneal puncture or a corneal laceration. In some embodiments, the cellulose hydrogel membrane is in the shape of a contact lens.

In some embodiments, the biocompatible cellulose hydrogel membrane is used to treat abrasions and surface damage to the eye caused by particulates and/or chemical exposure. In some embodiments, the cellulose hydrogel membrane is suitable for immediate field application by a non-health care professional. The cellulose hydrogel membrane can be applied immediately or shortly after the injury occurs or after a more extended period of time after the injury. The membrane can be administered to the subject by him or herself, or it can be administered to the subject by another.

The compositions of the invention can be administered in combination with existing wound care therapies or treatments. In some embodiments, the cellulose hydrogel membrane is contacted with a solution, e.g., a saline solution, once or more per day as a means to help maintain moisture at the wound site.

In some embodiments, the cellulose hydrogel membrane is replaced with a new cellulose hydrogel membrane intermittently, or every day, every 2 days, every 3 days, every 4 days, every 5 days, every 6 days or every 7 days or longer.

In some embodiments, the subject to be treated is a mammal, reptile, amphibian, fish or bird. Mammals include humans, mice, rats monkeys, and domestic animals such as dogs, cats, and the like.

By the term "effective amount" is meant an amount of cellulose hydrogel membrane (or the one or more bioactive agents therein) that produces the desired effect for which it is administered. The exact amount will depend on the purpose of the treatment, the subject to be treated, and will be ascertainable by a person skilled in the art using known methods and techniques for determining effective doses or amounts.

The cellulose hydrogel membrane can also include pharmaceutically and/or physiologically acceptable solutions, salts, buffers, antioxidants, preservatives, solubilizers, fillers, diluents, and other known substances. See, e.g., *Remington's Pharmaceutical Sciences,* 18th Edition, Mack Publishing Co. (1990), which is incorporated in its entirety herein by reference.

In some embodiments, the cellulose hydrogel membrane delivers an effective amount of the biologically active agent, in some embodiments, at a controlled rate. In some embodiments, the delivery is controlled for at least about 6 hours. In some embodiments, the cellulose hydrogel membrane continuously delivers an effective amount of the biologically active agent at a controlled rate for at least about 12 hours, at least about 24 hours, at least about 36 hours, at least about 48 hours, at least about 60 hours, at least about 72 hours, at least about 4 days, at least about 5 days, at least about 6 days, at least about 7 days, at least about 8 days, at least about 9 days, at least about 10 days, at least about 11 days, at least about 12 days, at least about 13 days or at least about 14 days or longer.

In some embodiments, the bioactive agent is bioavailable in less than about one hour after application of the cellulose hydrogel membrane. In some embodiments, in less than one-half hour. In some embodiments, the bioactive agent is bioavailable immediately or almost immediately after application of the cellulose hydrogel membrane. The composition can include one or more pharmaceutically acceptable excipients which can improve the stability and/or bioavailability of the bioactive agent.

In some embodiments, the cellulose hydrogel membrane of the invention can be configured or used for treatment of the eye of a subject. In some embodiments, the cellulose hydrogel membrane can be used to repair or replace the injured cornea and/or conjunctiva tissue of the eye. For example, the biocompatible material may be implanted in the treatment of corneal epithelial defects such as corneal ulcers (breaks in the outer layer of the epithelium of the cornea) and/or for ocular surface reconstruction. In some embodiments, the cellulose hydrogel membrane can be permanent or semi-permanent corneal replacement. In some embodiments, the cellulose hydrogel membrane for use in ocular wounds is in the shape of a contact lens.

In some embodiments, at least a portion of a damaged or diseased cornea of a subject is removed, and the cellulose hydrogel membrane of the invention is implanted in its place. The implant can be attached to the eye in any suitable fashion. In some embodiments, the implant is attached using sutures. In some embodiments, the cellulose hydrogel membrane is fixed in place by an adhesive that binds to both the eye and cellulose hydrogel membrane. In some embodiments the cellulose is functionalized to make it compatible with an ocular adhesive or with ocular tissue. Corneal implants incorporating a cellulose hydrogel membrane of the present invention may be provided in a shape corresponding to all or a portion of a native cornea. The implant can be provided as single-layer or multiple-layer of cellulose hydrogel material to provide the desired thickness.

Application of the teachings of the present invention to a specific problem is within the capabilities of one having ordinary skill in the art in light of the teaching contained herein. Examples of the compositions and methods of the invention appear in the following non-limiting Examples.

EXAMPLES

Example 1-1

Cellulose Gel Synthesis

Seven different types of cellulose were evaluated to determine suitable material for synthesis of a cellulose hydrogel.

TABLE 1

| Cellulose Type | Avicel PH 101 | Avicel PH 102 | Avicel PH 105 | Avicel PH 200 | Aldrich Product #310697 | Aldrich Product #435236 | Bacterial Cellulose (Xylos) |
|---|---|---|---|---|---|---|---|
| Origin | Plant fiber | Plant fiber | Plant fiber | Plant fiber | Cotton Linters | Cotton Linters | *Acetobacter xylinum* |
| Particle size (microns) | 50 | 90 | 20 | 180 | 20 | ~100 | 20 nm × 50 nm × 100 μm |
| Density (g/cm$^3$) | 0.26-0.31 | 0.28-0.33 | 0.20-0.30 | 0.29-0.36 | 0.5 | 0.6 | 1.6 |
| Moisture Content (%) | 3-5 | 3-5 | <5 | 2-5 | | | |

The cellulose hydrogel was synthesized by activating 2-5 grams of cellulose powder in 100 ml N,N-dimethylacetamide (DMAc), and stirring (for example, at 350 rpm) for 24 hours. In a separate beaker, 8 grams of LiCl was dissolved in 100 ml DMAc, and stirred at 350 rpm. The DMAc was decanted from the activated cellulose powder and the LiCl/DMAc solution was poured onto the cellulose, and stirred for 10 minutes. The resulting transparent solutions were poured into desired molds and allowed to "gel" overnight. The gels were de-molded and washed in running water for several hours.

Figures 1A, 1B:
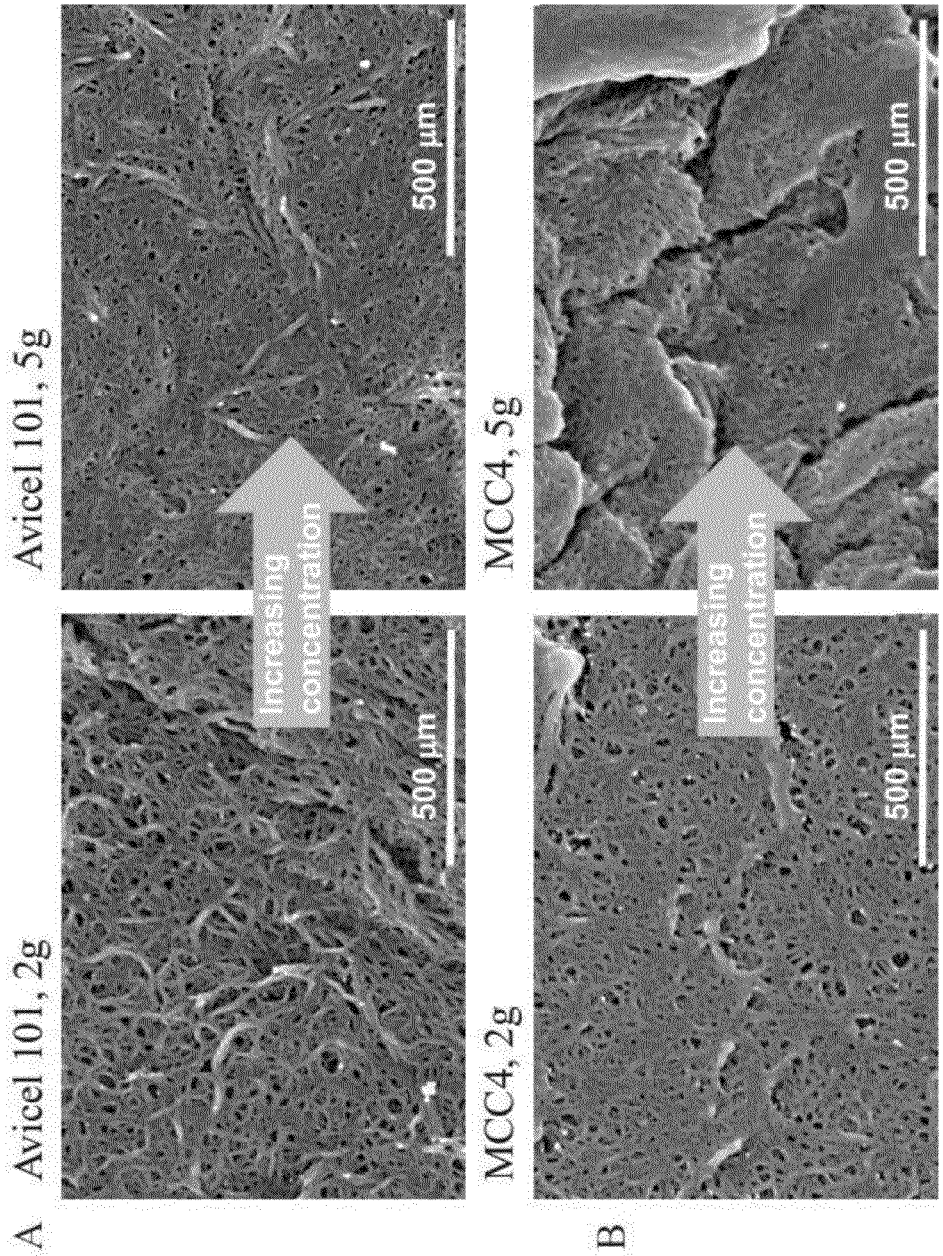
Figure 2:
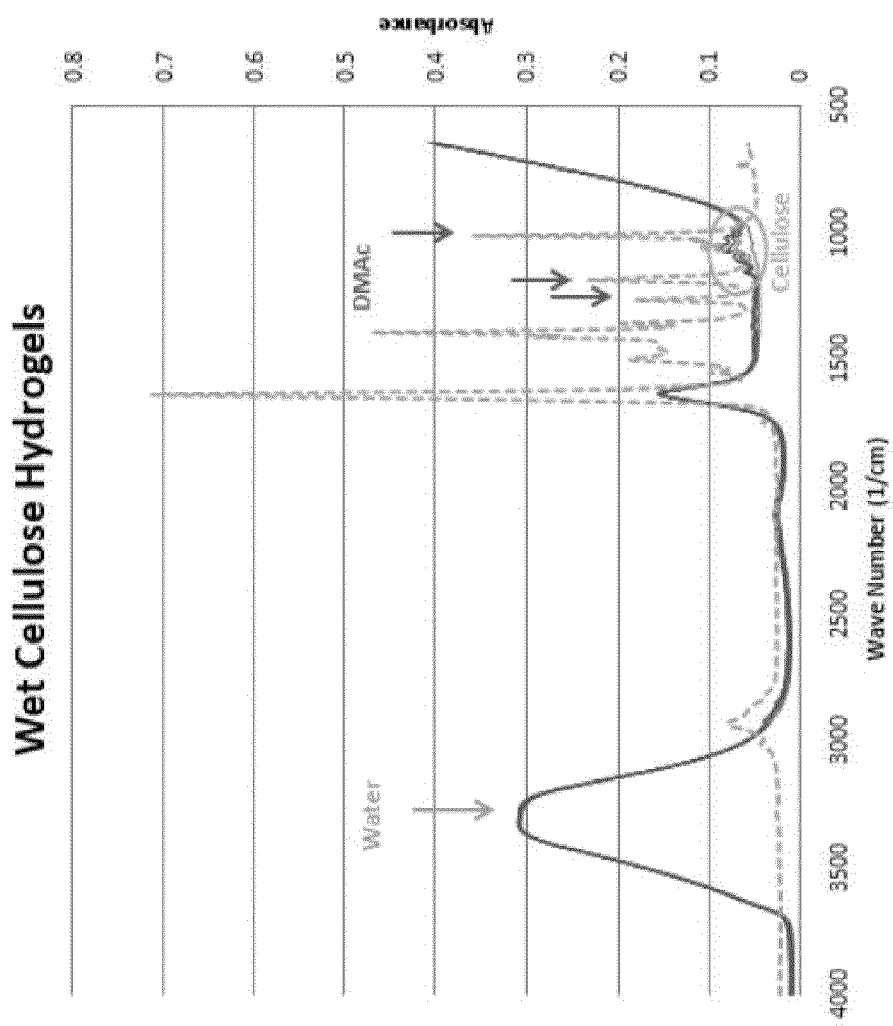
Figures 4A, 4B:
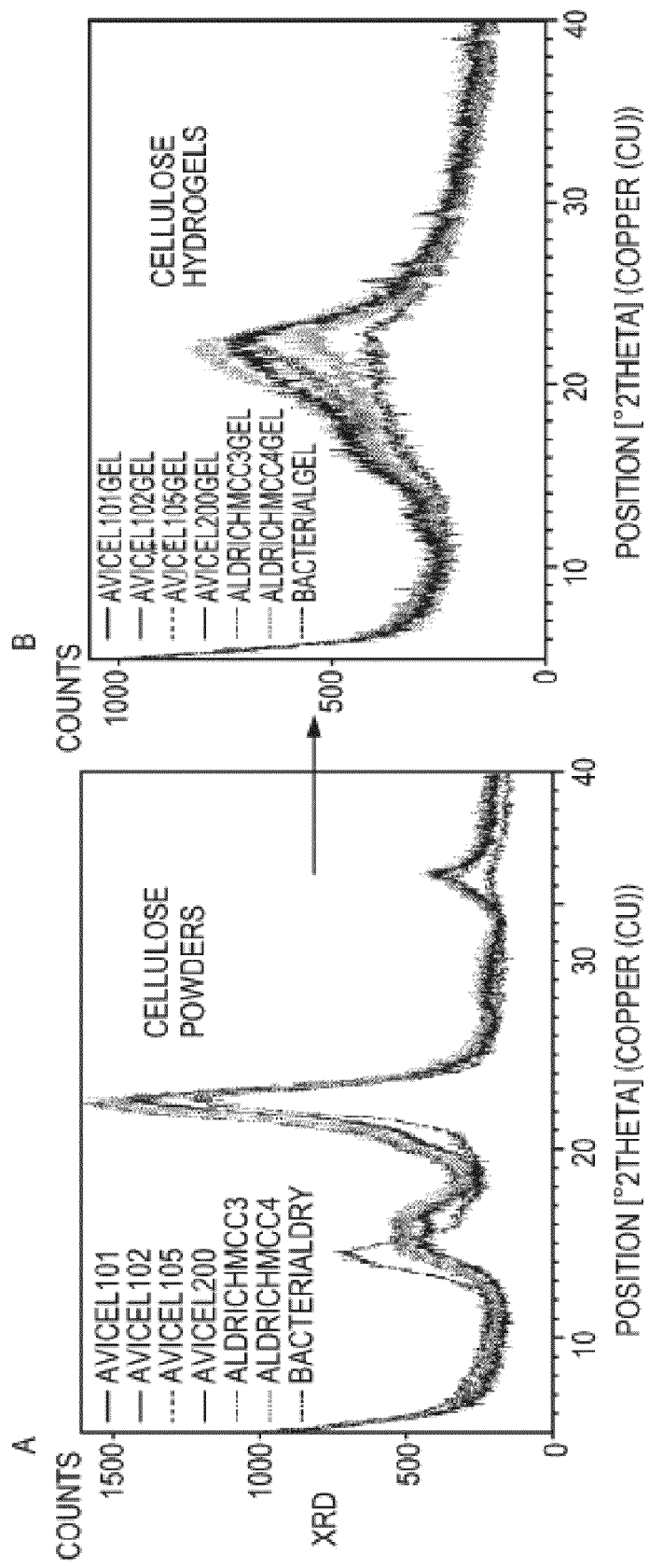

The hydrogels were subjected to various analyses, including Fourier Transform Infrared Spectroscopy (FTIR), X-ray diffraction (XRD) and thermogravimetric analysis (TGA) to determine 1) whether there were any chemical differences between different varieties of cellulose, 2) how different phases of cellulose compare (raw powder, wet hydrogel, dry gel, re-wet gel) and 3) whether the gels were washed successfully. As shown in FIGS. 2 and 4, there were no significant chemical differences between the varieties of cellulose and the washing procedure was successful.

Figure 5:
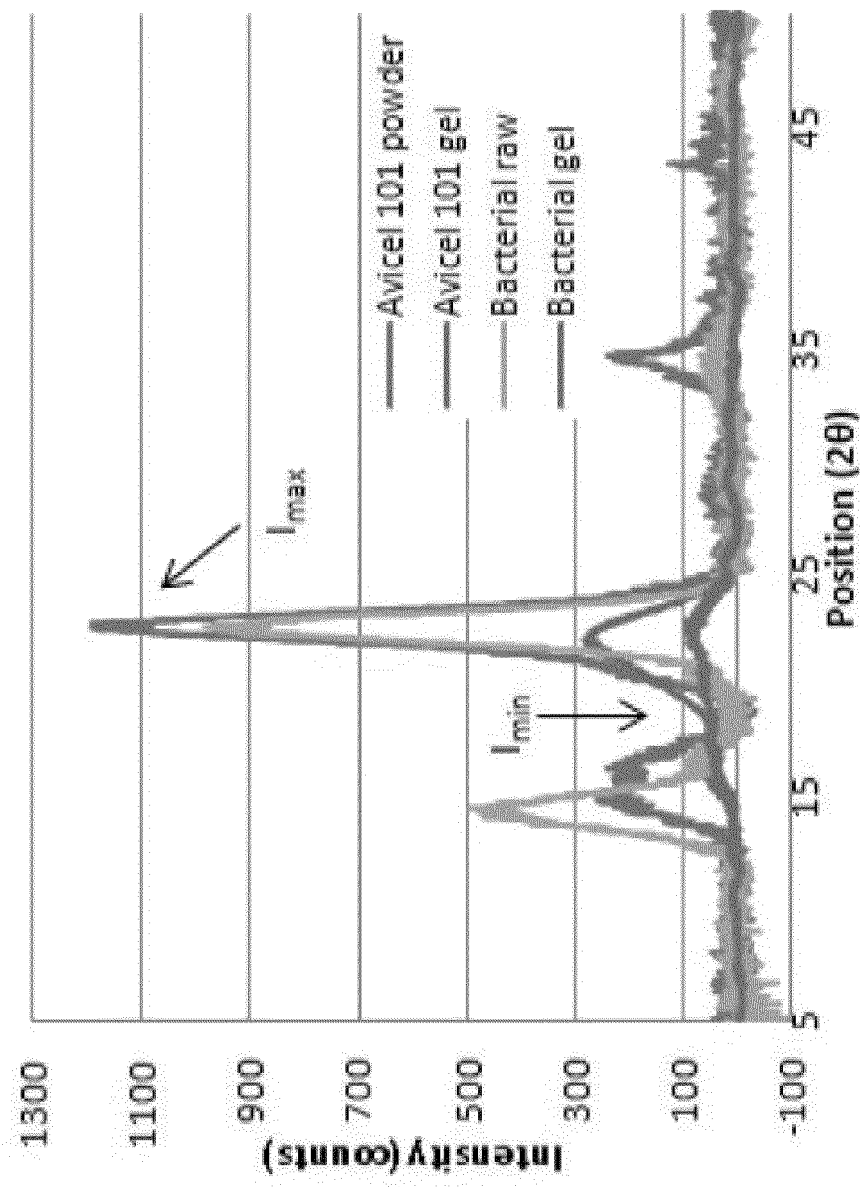
FIG. 5 shows X-ray diffraction analysis of cellulose raw powder and hydrogel phases.

X-ray diffraction analysis was performed to determine whether there were any differences in crystallinity between the varieties of cellulose and how crystallinity compared between the raw powder and hydrogel phases. The degree of crystallinity ($I_c=1-(I_{min}/I_{max})$) was calculated according to Buschle-Diller and Zeronian, *J Appl Polym Sci*, 45, 967 (1992). The hydrogels are less crystalline than the raw powders (FIG. 5).

The ratio of cellulose I to cellulose II was also investigated according to the method of Gindl and Keckes, *Polymer* 46, 10221-10225 (2005). The ratio of cellulose I/II is significantly lower in the hydrogel phase, and bacterial cellulose has a much greater cellulose II ratio in the raw phase than the other varieties. The results are shown in Table 2, below.

TABLE 2

| | Index of Crystallinity | | Cellulose I/II | |
|---|---|---|---|---|
| Type | Raw | Gel | Raw | Gel |
| Avicel 101 | 1.029 | 0.861 | 5.423 | 1.337 |
| Avicel 102 | 1.017 | 0.809 | 5.692 | 2.169 |
| Avicel 105 | 1.015 | 0.868 | 3.761 | 2.467 |
| Avicel 200 | 1.022 | 0.753 | 5.117 | 1.230 |
| Aldrich 310697 | 1.032 | 0.850 | 5.732 | 1.175 |
| Aldrich 435236 | 1.032 | 0.911 | 5.244 | 1.335 |
| Bacterial | 1.021 | 0.602 | 10.347 | 1.262 |

The water content of various cellulose hydrogels was determined by thermal gravimetric analysis.

Figure 3A:
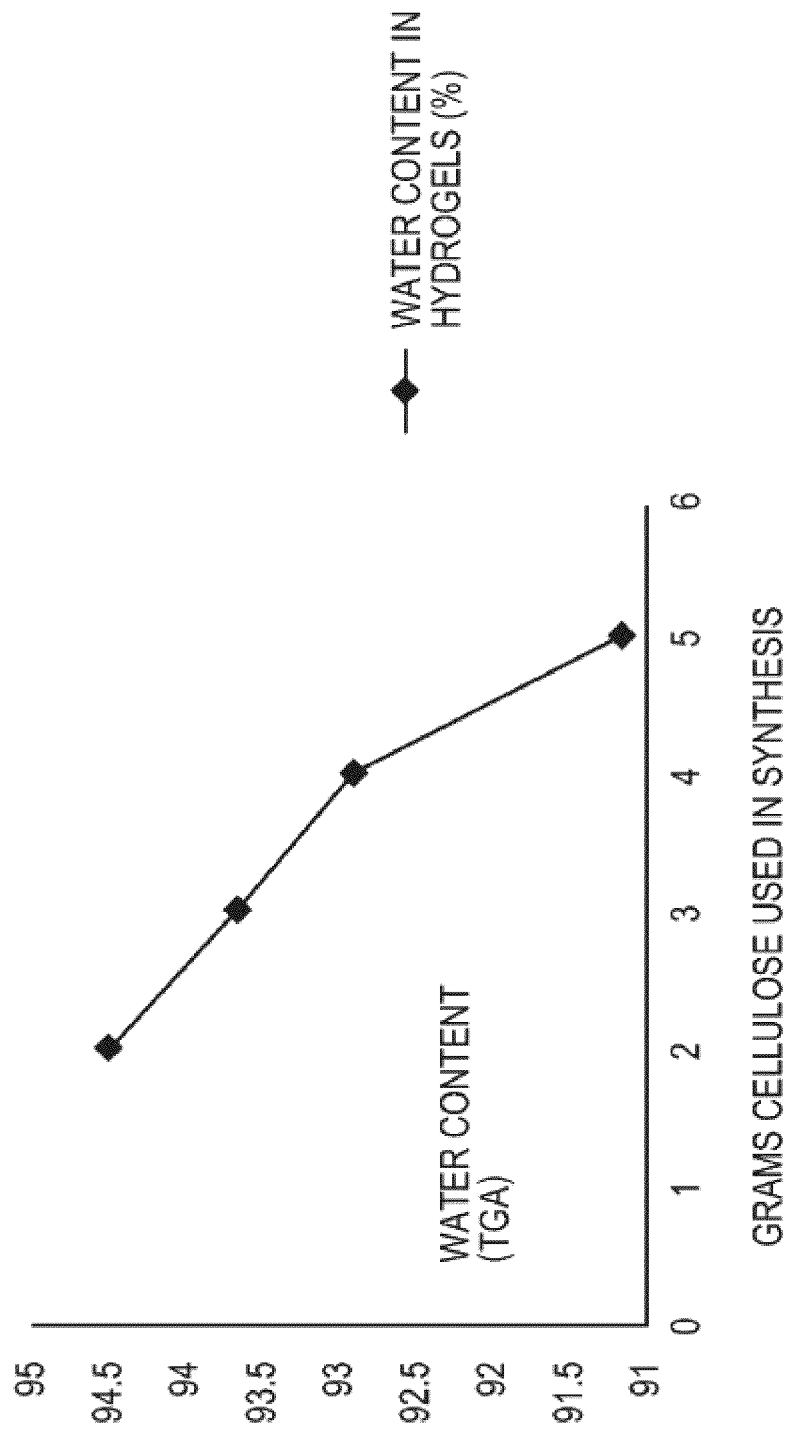
Figure 3B:
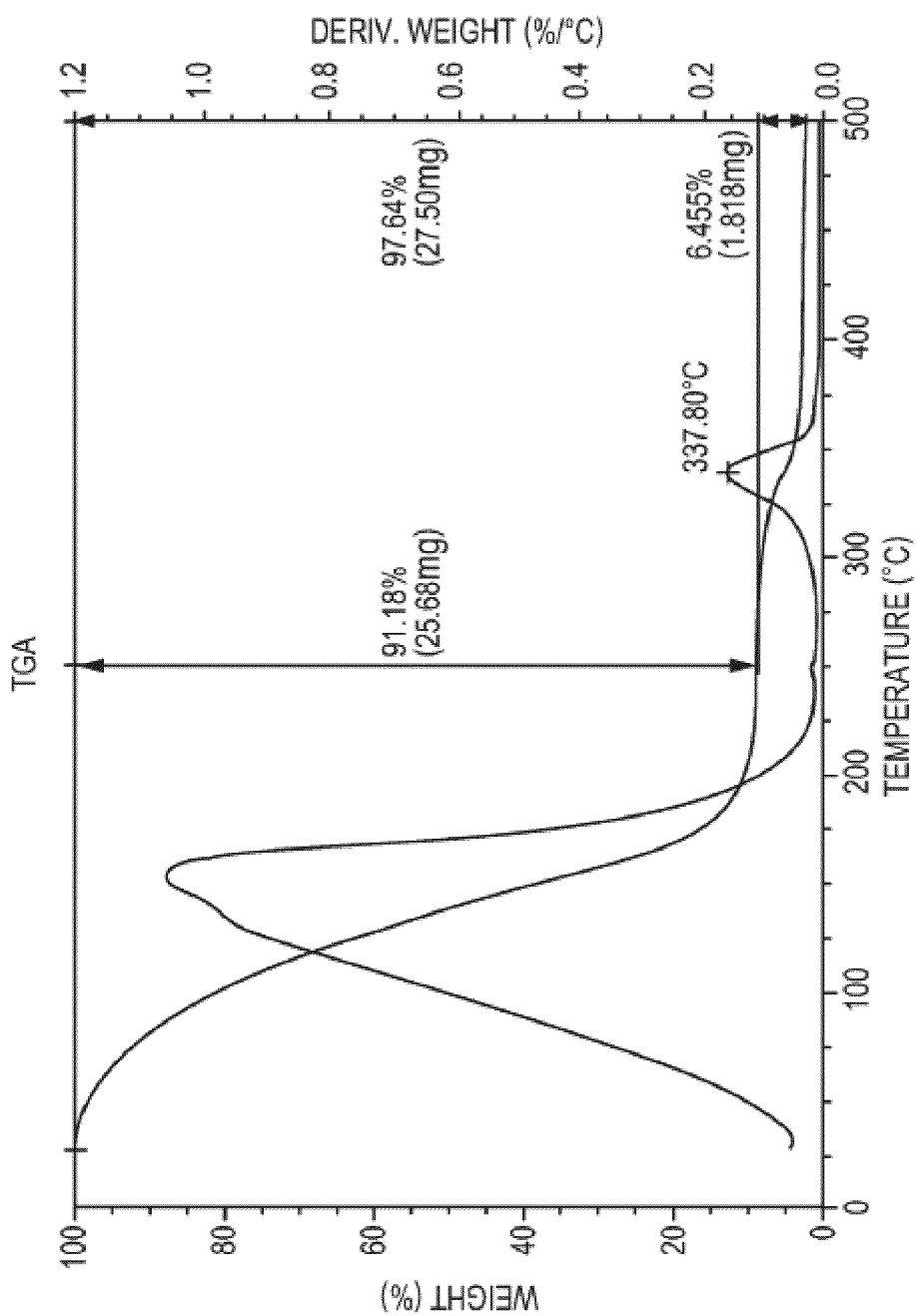

Cellulose hydrogels prepared under different concentrations (2, 3, 4 and 5 g) were analyzed by TA instrument Q5000 Thermal Gravimetric Analyzer (TGA). All samples were heated from RT to 500 C at 20 C/min under N2 purge. During the test, sample weight change versus temperature was recorded. Derivatives of wt with regard to temperature (dWt/dT) was used to probe the peak temperature for each thermal transition. The mass lost during the temperature increase reflected the water content. As shown in FIGS. 3A-B, the range of water content obtained for the various wet hydrogels was about 91-95%. TGA analysis comparing dried/re-wet and never dried hydrogels is shown in FIGS. 14A-B.

Figure 6:
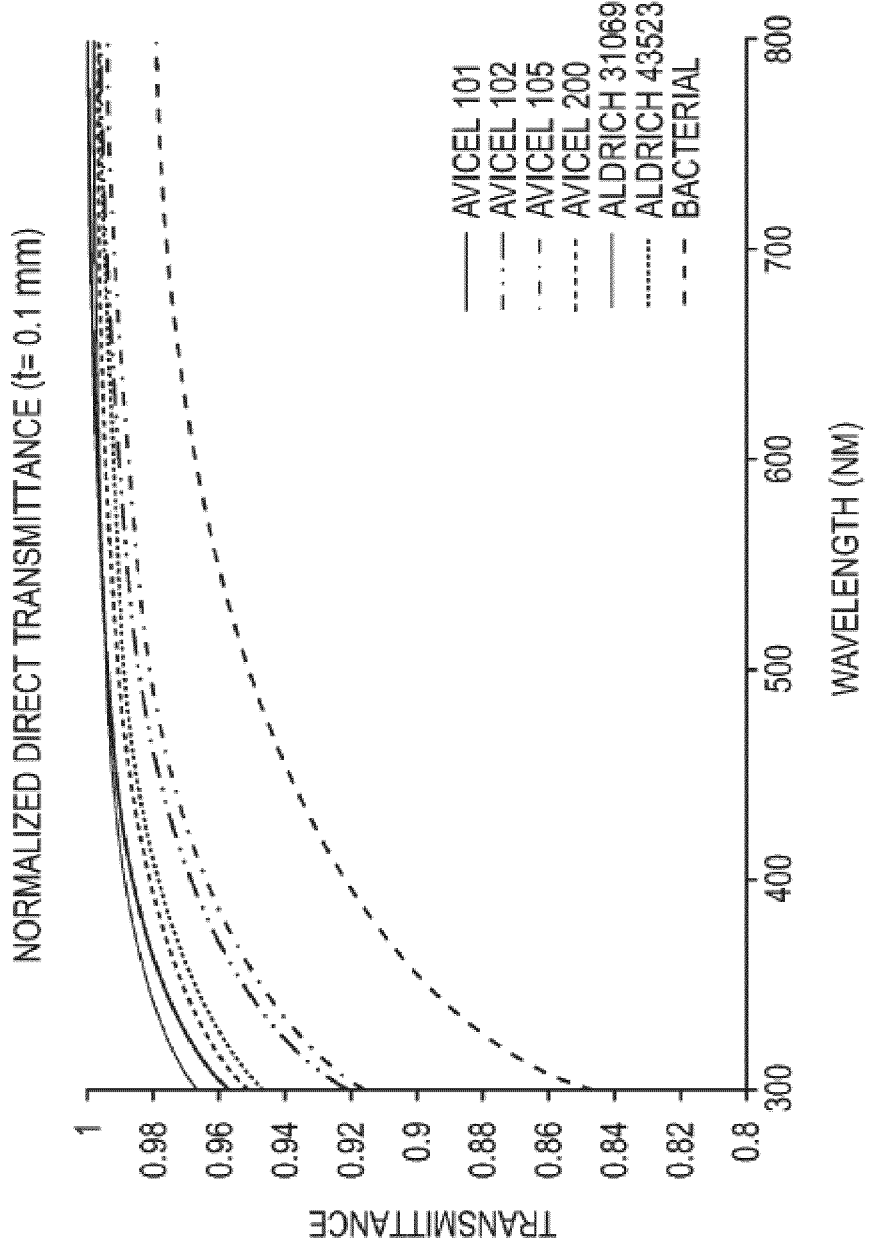
FIG. 6 shows transparency and refractive index data for 100 micron thick cellulose hydrogels.

The transparency of 100 micron thick cellulose hydrogels was also determined. Percent transmittance values were generated at a wavelength of 550 nm. The transparency of all cellulose hydrogels exceeded 95% in the visible range. The results are shown in FIG. 6.

The refractive index of the cellulose hydrogels was measured. The results are shown in Table 3, along with a comparison with various commercially available contact lenses.

TABLE 3

| Material | N |
|---|---|
| Avicel 101 | 1.3405 |
| Avicel 102 | 1.3420 |
| Aldrich 310697 | 1.3405 |
| Aldrich 435236 | 1.3402 |
| Avicel 105 | 1.3415 |
| Avicel 200 | 1.3435 |
| Soflens (Bausch & Lomb) | 1.430 |
| Hoya Soft (Hoya) | 1.450 |
| O$_2$ (Menicon) | 1.481 |
| Snoflex 50 (Smith & Nephew) | 1.410 |
| Gelflex 75 (W.A.C.L.M.) | 1.376 |
| Parabolar (Wohik) | 1.493 |

Example 1-2

Mechanical Properties of Cellulose Hydrogels

1. Tear Strength

The tear strength of cellulose hydrogels in three different states (hydrated, dehydrated, and rehydrated) was characterized. All samples were made to conform to the geometry stated in ASTM standard D 624-00, sample type C. Samples in the hydrated state were made by pouring the cellulose+LiCl/DMAc solution into a mold with the appropriate sample geometry. Cheesecloth was placed in the ends of the mold before pouring to assist in gripping the hydrated gels during testing. Hydrated samples were allowed to gel overnight, washed in running tap water for 2-4 hours, soaked in tap water with frequent water exchange for 24-48 hours, and stored in tap water. Sheets of cellulose hydrogel were made by pouring the cellulose LiCl/DMAc solution onto a glass plate and allowing to gel overnight. Sheets were dehydrated between glass plates lined with Teflon film in an oven above 100° C.

for approximately 5 hours. The sheets were then rehydrated in tap water for several hours. Samples were cut from rehydrated sheets by hand and either returned to water (rehydrated) or allowed to air dry (dehydrated). The thickness of all samples was measured prior to testing in three locations near the site of tearing (at the apex, above and below the apex) and the three values were averaged to obtain the sample thickness. All samples were tested using a 500N capacity tabletop mechanical testing system (#5942R4910, Instron) with a 5N maximum static load cell (#102608, Instron). Pneumatic side action grips were used to secure the samples (#2712-019, Instron). Samples were tested with a constant extension rate of 2 mm/min until failure. The tear strength was calculated as the force at failure divided by the average thickness (N/mm). Two different cellulose materials (Avicel 101 and Aldrich 4) and two different concentrations (2 g and 5 g) were characterized and compared in each state (hydrated, dehydrated, and rehydrated). See FIG. 17. Tear strength of typical contact lenses is 0.37-0.49 N/mm.

2. Suturability Characterization

Methods

The suture retention strength of cellulose hydrogels was characterized as a measure of their surgical feasibility. Cellulose hydrogels in three states (hydrated, dehydrated, and rehydrated) were characterized. Samples were cut from cellulose sheets as described above. Samples were cut in rectangles 2 cm×4 cm. The testing procedure described by Trowbridge et al. was modified for use in this study (Trowbridge, E. A., Lawford, P. V., and Crofts, C. E. Pericardial heterografts: a comparative study of suture pull-out and tissue strength. *J. Biomed. Eng.*, 11 (1989) 311-14). All samples were tested using a 500N capacity tabletop mechanical testing system (#5942R4910, Instron) with a 5N maximum static load cell (#102608, Instron). Pneumatic side action grips were used to secure the samples (#2712-019, Instron). Before testing, the thickness of each sample was measured at three points along one of the short edges (designated the top edge). The sample was then secured in the stationary (bottom) pneumatic grip, with half of the sample inside of the grip, and a suture was threaded through the sample once in the center of the sample with a bite size of 2 mm from the top edge. Ethicon Ethilon 10-0 ophthalmic sutures were used (7756G and 7711G, Ethicon, Inc.). Both ends of the suture were secured in the movable (top) pneumatic grip. FIG. 22 shows a diagram of the sample setup, and FIG. 23 shows results of the testing. Samples were tested with a constant extension rate of 10 mm/min until failure. The suture retention strength was taken to be the force at failure divided by the average sample thickness (N/mm).

3. Puncture Testing

Puncture strength was measured according to the method described by Radebaugh et al. (Radebaugh et al., *Int J Pharmaceutics* 45, 1988, p 39-46). A schematic of their setup is shown in FIG. 18A, and the fixture used for testing is shown in FIG. 18B. Rather than fixing the hydrogel between two plates using screws, which can pinch or tear the gel, the hydrogels were secured to the fixture with cyanoacrylate. A hemispherical probe with a 2 mm diameter was lowered onto the gel at a rate of 2 or 10 mm/min.

Elongation to puncture was measured as $$\varepsilon_p(\%) = \frac{([R]^2 + [D]^2)^{1/2} - R}{R} \cdot 100,$$

puncture strength as $$\sigma_{puncture}(kPa) = \frac{F}{A_{cs}},$$

and energy to puncture as $$\Delta E_p(J/cm^3) = \frac{\int F \cdot D}{V_c},$$

where F=force and all other variables are defined as in FIG. 18C.

4. Tensile Strength

The tensile strength of the prepared ("wet") cellulose hydrogels was measured using a 500N capacity tabletop mechanical testing system (#5942R4910, Instron) with a 5N maximum static load cell (#102608, Instron). Pneumatic side action grips were used to secure the samples (#2712-019, Instron). A constant extension rate of 2 mm/min until failure was used and the tensile strength was calculated from the stress vs. strain data plots. Samples were prepared by pouring the cellulose LiCl/DMAc solution into a "dogbone" mold as shown in FIG. 8. Cheesecloth was placed in both ends of the mold before pouring to assist in gripping the gels during testing. Samples were allowed to gel overnight, washed in running tap water for 2-4 hours, soaked in tap water with frequent water exchange for 24-48 hours, and stored in tap water until use. Prior to testing, the width and thickness of the hydrogel at the center of the dogbone, as well as the gauge length were measured for all samples. Initially, six different cellulose materials (Avicel 101, Avicel 102, Avicel 105, Avicel 200, Aldrich 310697, and Aldrich 435236) at a concentration of 2% (w/v dry cellulose to LiCl/DMAc solution) were characterized. Avicel 101 and Aldrich 435236 were further characterized at varying concentrations (2%-5%) and varying stir times in the LiCl/DMAc solution (5-30 minutes).

Example 1-3

Transparency Properties of the Cellulose Hydrogels

The transmittance of the cellulose hydrogels was measured in the range of wavelengths from 250 to 800 nm using a Perkin-Elmer Lambda 9500 series UV-visible spectrophotometer. As transmittance is dependent upon thickness, the thickness of each sample was measured with calipers prior to loading the sample in the spectrophotometer. Transmittance values were then normalized to a thickness of 100 μm according to $$F_{T-corr}(\lambda, t_2) = [e^{-\sigma_t(\lambda)t_1}]^{\frac{t_2}{t_1}} = [F_{T-corr}(\lambda, t_1)]^{\frac{t_2}{t_1}},$$

where $t_1$=actual specimen thickness, $t_2$=thickness to which transmittance measurements were normalized.

Example 1-4

Oxygen Permeability Properties of Cellulose Hydrogels

Oxygen permeability of the cellulose and collagen materials can be determined using a polarographic method. This method directly measures the number of oxygen molecules diffusing though the material by measuring an electric current generated by the reduction of oxygen at the cathode. In a single polarographic determination, for example, four samples of the same material with different thicknesses can be used. This results in a linear relation between the inverse of oxygen transmissibility and the sample thickness. The sample is placed onto the surface of the electrode (cell), fixed gently by pressing toward the electrode and retained with an o-ring. Then, a saline solution (0.9% NaCl, pH 7.4) is poured into the reservoir on the material, and the system is ready for measuring the electric current. The system is held in a humidity chamber at 35° C. with high humidity (the polarographic cell and the saline solution are in the humidity chamber prior the measurement to achieve equilibrium conditions). The saline solution and the sample are saturated with atmospheric oxygen. To remove the oxygen, nitrogen gas is bubbled through a glass flit while monitoring current, until the current decreases to nearly zero. Once most of the oxygen is removed, air is bubbled into the solution, and the increase in electric current is observed as the oxygen molecules react with the cathode. The current is recorded until it reaches a stationary state.

Example 1-5

Molded Contact Lens from Cellulose Sheet

Two drops of PBS buffer are added to the cavity in the bottom half of a contact lens mold, an embodiment of which is illustrated in FIG. 24. The cavity is covered with a 2 cm×2 cm sheet of cellulose (which can be substituted with a cellulose hydrogel of the invention). 1-2 more drops of PBS buffer are placed on top of the cellulose. The top half of the contact lens mold is then put over the bottom half. A spring clamp is then applied to keep the halves together. The mold is then placed in a humidity chamber at 40% relative humidity and 40° C. After 48 hours, the clamp is removed and the mold is opened. The excess cellulose and gel is then trimmed and removed as necessary. The lens is then stored in PBS buffer.

Example 2-1

A series of experiments were conducted to evaluate the in vivo biocompatibility and related physical properties of cellulose-based hydrogel contact lenses, according to certain embodiments of the present invention, for potential use as a corneal bandage.

Cellulose hydrogels were prepared by activating the cellulose powder (or dried bacterial cellulose (BC) pellicle) in 100 mL N,N-dimethylacetamide (DMAc) with stirring for 24 hours, after which 8 g of LiCl was added with continued stirring and gentle heating until the solution became clear. The resulting solution was poured into molds of appropriate dimensions and allowed to gel. The gelled samples were gently washed in water to remove excess LiCl/DMAc and stored in water prior to characterization.

Oxygen Permeability Method and Results

Hydrogel oxygen permeability was measured using the polarographic method. The samples were fixed in place on a flat polarography cell having a gold cathode surrounded by a silver anode. The system was held in a humidity chamber at 35° C. with humidity >90%. A 0.9% saline solution (pH 7.4), was used in the reservoir. The system was saturated with nitrogen to remove the oxygen as noted by the current being nearly zero. Next, air was bubbled through a glass frit into the solution and the change in current recorded. Three reference materials were used to develop a calibration curve from which the permeability of the samples was calculated and corrected for boundary layer and edge effects. FIG. 25A illustrates a diagram of the polarographic cell used for the measurement of the oxygen permeability of the hydrogels. FIG. 25B shows the calibration curve from which the permeability of the samples was calculated.

The measured oxygen permeability of the hydrogels is in the range reported for commercial contact lenses and thus would allow sufficient oxygen transport for ocular surface applications. As shown in FIG. 25C, the average oxygen permeability for the hydrogels ranged from 60 to 94 Dk, which is within the range of commercial contact lenses.

In Vivo Biocompatibility: Methods & Results

Hydrogels from the three different materials (Avicel 101, MCC4, and BC) and a conventional polymethylmethacrylate (PMMA) contact lens were evaluated for acute immune response and cytotoxicity. The gels were implanted in 6 week old female rats. Under inhalation anesthesia (Isoflurane), a 1.5 cm incision was made on the back of rats to insert each implant. After implantation, each incision was closed by 4-0 nylon suture. The rats were sacrificed 3 or 7 days after surgery and each specimen was cultured under aseptic techniques. Sections (5 μm) of dehydrated, paraffin-embedded specimens were stained with hematoxylin and eosin (H&E) according to standard method. As shown in FIG. 26A-26H (scale bar: 100 microns), H&E staining images show that after 7 days, the immune responses to the cellulose implants were less severe than the commercial contact lens, in which the region identified as "M" indicates the location of the material. In particular, FIG. 26A (3 days after implantation) and 26E (7 days after implantation) show the H&E staining images of hydrogel implants and surrounding tissue with Avicel 101. FIG. 26B (3 days after implantation) and 26F (7 days after implantation) show the H&E staining images of hydrogel implants and surrounding tissue with bacterial cellulose (BC). FIG. 26C (3 days after implantation) and 26G (7 days after implantation) show the H&E staining images of hydrogel implants and surrounding tissue with MCC4. FIG. 26D (3 days after implantation) and 26H (7 days after implantation) show the H&E staining images of conventional PMMA material and surrounding tissue.

Endotoxin: Method & Results

The starting materials and their resulting hydrogels were subjected to endotoxin analysis both with and without a Glucan blocker (Lonza, Walkersville, Md.). Initial results suggested endotoxins were introduced via handling the hydrogels during synthesis. Thus, three important changes were made to the synthesis procedure: 1) all glassware was depyrogenated using dry heat; 2) all water used was sterile filtered (0.2 um filter); and, 3) all synthesis steps were carried out in a laminar flow hood. These simple changes resulted in a 95% reduction in endotoxin level. More careful handling of the final gels reduced the endotoxin levels an additional 97% which reached the acceptable levels for medical devices (<0.05EU/ml). The BC had high levels of endotoxin despite the aseptic handling techniques which was likely due to incomplete depyrogenation of the cultured pellicles.

Contact Lens Fabrication

Avicel 101 was chosen as the cellulose material for contact lens development based on the combined results of the previous results. As such, a contact lens shaped mold was designed and fabricated. Using the methods described above, contact lenses were prepared for in vivo testing.

One week prior to the study start, the nictitating membranes of four male New Zealand White rabbits were fixed. A commercial lens, Hydrokone® (Hioxifilcon A: Benz G5X p-GMA/HEMA), was used as a control and was placed in the rabbits' right eye and the experimental cellulose lens was placed in the rabbits' left eye. Lenses were evaluated for fit, abrasion and toxicity (ISO 9394). The rabbits were monitored clinically each day using the Drazie scale and weekly via slit lamp examination and fluorescein staining. The rabbits were sacrificed after 22 days for pathological examination. Each specimen was cultured under aseptic techniques. Sections (5 μm) of dehydrated, paraffin-embedded specimens were stained with (H&E), Masson's trichrome, and PAS according to standard methods.

The cellulose contact lenses were more stable but slightly more irritating than the COTS lenses on the corneal surface. There was no abrasion of the corneal surface from either lens after circular rubbing 50 times. After 21 days of wear for a minimum of 7 hours per day, the experimental eyes showed no corneal opacity, iris lesions, conjunctival chemosis, or aqueous flare. The histology suggests a flattening of the corneal surface. This and the increased redness is likely not due to the material, but to its geometry, and could be improved via manufacturing optimization. FIG. 27A shows the lens fit (far left) and abrasion (far right) after circular rubbing 50 times. FIG. 27B shows the histology after 21 days of wear with a minimum of 7 hours per day of wear.

The foregoing results demonstrate, for example, cellulose hydrogels were synthesized using aseptic methods to result in lenses with desirable material properties, including high oxygen permeability and low endotoxin levels. In vivo biocompatibility was demonstrated using a rat subcutaneous implant model. Cellulose hydrogel contact lens were successfully tested in vivo and showed no evidence of corneal toxicity for 21 days, though the fit needs to be improved. This material shows promise for use as a temporary corneal bandage, for example in the combat setting, until hospital treatment can be received.

All references, including publications, patent applications, and patents, cited herein are hereby incorporated by reference to the same extent as if each reference were individually and specifically indicated to be incorporated by reference and were set forth in its entirety herein.

These and other modifications and variations to the present invention may be practiced by those of ordinary skill in the art without departing from the spirit and scope of the present invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

That which is claimed:

1. A wet cellulose hydrogel, comprising: a cellulose content from about 1% to about 10% by weight; said cellulose hydrogel comprising (a) a tear strength of from about 0.8 N/mm to about 3 N/mm and (b) a Young's modulus of from about 900 kPa to about 1600 kPa; said cellulose hydrogel further comprising one or more properties selected from the group consisting of (i) a tensile strength in the range of from about 50 kPa to about 4000 kPa; (ii) a transparency that exceeds 85% at 550 nm; and (iii) an oxygen permeability from about 55 to about 150 Dk.

2. The hydrogel of claim 1, wherein the cellulose content comprises from about 2% to about 7%.

3. The hydrogel of claim 1, wherein cellulose content comprises from about 2% to about 5%.

4. The hydrogel of claim 1, wherein the cellulose content comprises a denaturation temperature of at least about 70° C.

5. The hydrogel of claim 4, wherein the cellulose hydrogel comprises each of the following (1) the tensile strength comprises from about 625 kPa to about 3500 kPa; (2) the transparency exceeds 90% at 550 nm; (3) the denaturation temperature exceeds 200° C. and is less than 330° C.; and (4) the oxygen permeability comprises from about 55 to about 130 Dk.

6. The hydrogel of claim 5, wherein the denaturation temperature exceeds about 250° C. and less than about 300° C.

7. The hydrogel of claim 1, wherein the hydrogel further comprises a strain to failure of from about 40% to about 160%.

8. The hydrogel of claim 1, wherein the hydrogel further comprises a suture retention strength of from about 0.1 N/mm to about 3.5 N/mm.

9. The hydrogel of claim 1, wherein the hydrogel further comprises a puncture resistance of from about 100 kPa to about 300 kPa.

10. The hydrogel of claim 1, wherein the hydrogel is in the shape of a contact lens.

11. The hydrogel of claim 1, wherein the cellulose is from a source selected from the group consisting of plant, wood pulp, cotton pulp, microbial, and combinations thereof.

12. The hydrogel of claim 1, wherein the hydrogel comprises one or more cellulose fiber layers.

13. The hydrogel of claim 1, wherein the transparency of the hydrogel is at least 95% at 550 nm.

14. The hydrogel of claim 1, wherein the hydrogel has a thickness of from about 50 to about 250 microns.

15. The hydrogel of claim 1, wherein the hydrogel has a refractive index of from about 1.30 to about 1.50.

16. The hydrogel of claim 1, wherein the hydrogel comprises bacterial cellulose.

17. A wet cellulose hydrogel, comprising: a cellulose content from about 1% to about 10% by weight; said cellulose hydrogel comprising (a) a tear strength of from about 0.8 N/mm to about 3 N/mm; (b) Young's modulus of from about 900 kPa to about 1600 kPa; and (c) an oxygen permeability from about 55 to about 150 Dk.

18. The hydrogel of claim 17, wherein said hydrogel comprises a tear strength of from about 1.0 N/mm to about 3 N/mm and a Young's modulus of from about 1000 kPa to about 1600 kPa.

19. The hydrogel of claim 17, wherein said hydrogel comprises a tear strength of from about 1.5 N/mm to about 3 N/mm.

20. The hydrogel of claim 19, wherein the hydrogel comprises a Young's modulus of from about 1000 kPa to about 1600 kPa.

* * * * *